(12) United States Patent
Kishimoto et al.

(10) Patent No.: US 7,303,566 B2
(45) Date of Patent: Dec. 4, 2007

(54) DECOMPRESSION-COMPENSATING INSTRUMENT FOR OCULAR SURGERY, INSTRUMENT FOR OCULAR SURGERY PROVIDED WITH THE SAME AND METHOD OF OCULAR SURGERY

(75) Inventors: Makoto Kishimoto, 10-8, Moriyama 1-chome, Moriyama-shi, Shiga 524-0022 (JP); Yoshiyuki Kimura, Kakogawa (JP)

(73) Assignees: Makoto Kishimoto, Moriyama-shi (JP); Senju Pharmaceutical Co., Ltd., Osaka-shi (JP)

( * ) Notice: Subject to any disclaimer, the term of this patent is extended or adjusted under 35 U.S.C. 154(b) by 142 days.

(21) Appl. No.: 10/512,867

(22) PCT Filed: Jun. 20, 2003

(86) PCT No.: PCT/JP03/07846

§ 371 (c)(1),
(2), (4) Date: Nov. 15, 2004

(87) PCT Pub. No.: WO04/000181

PCT Pub. Date: Dec. 31, 2003

(65) Prior Publication Data

US 2006/0058811 A1    Mar. 16, 2006

(30) Foreign Application Priority Data

Jun. 21, 2002   (JP) .............................. 2002-182045

(51) Int. Cl.
*A61F 9/00* (2006.01)
*A61B 17/22* (2006.01)

(52) U.S. Cl. .......................... 606/107; 604/22; 604/27

(58) Field of Classification Search ................. 604/31, 604/65–67, 245, 22, 27, 28, 43, 42; 606/107; 141/21, 25
See application file for complete search history.

(56) References Cited

U.S. PATENT DOCUMENTS 3,902,495 A * 9/1975 Weiss et al. .................. 604/22
4,701,305 A * 10/1987 Hattori et al. ................ 422/73
5,413,556 A * 5/1995 Whittingham ............... 604/22

(Continued)

FOREIGN PATENT DOCUMENTS

EP        862902 A2    9/1998

(Continued)

*Primary Examiner*—Glenn K. Dawson
*Assistant Examiner*—Kathleen Sonnett
(74) *Attorney, Agent, or Firm*—Kratz, Quintos & Hanson, LLP

(57) ABSTRACT

The present invention relates to a decompression-compensating instrument for use in intraocular surgery, wherein a perfusate is supplied to an affected part of an eye via a supply channel at a predetermined pressure, and the perfusate is aspirated via an aspiration channel together with the affected tissues that are to be removed, the decompression-compensating instrument supplying the perfusate into the affected part when the internal pressure of the affected part is excessively lowered, and being constructed so as to be connectable to a point midway along the supply channel and comprising a storage-member that forms a chamber that is closable except for an opening from which the perfusate to be supplied to the supply channel flows, the capacity of the storage member being 7 $cm^3$ to 22 $cm^3$.

17 Claims, 21 Drawing Sheets

U.S. PATENT DOCUMENTS

| | | | |
|---|---|---|---|
| 5,476,448 A | * | 12/1995 | Urich .......................... 604/22 |
| 5,725,832 A | * | 3/1998 | Gundelsheimer ........... 422/102 |
| 5,827,233 A | * | 10/1998 | Futagawa et al. ........... 604/232 |
| 6,042,586 A | * | 3/2000 | Kawano et al. ............. 606/107 |
| 6,723,065 B2 | * | 4/2004 | Kishimoto .................. 604/43 |

FOREIGN PATENT DOCUMENTS

| JP | 2001-170102 | 6/2001 |
|---|---|---|

* cited by examiner (a)

(b)

(c)

(a)

(b)

(c)

(a)

(b)

(c)

Explanation of Symbol

Fig. 14

A: Start of aspiration
    B: Blocking of the aspiration tube
    C: Blocking of the aspiration tube is removed

Fig. 15

A: Start of aspiration
    B: Blocking of the aspiration tube
    C: Blocking of the aspiration tube is removed

US 7,303,566 B2

DECOMPRESSION-COMPENSATING INSTRUMENT FOR OCULAR SURGERY, INSTRUMENT FOR OCULAR SURGERY PROVIDED WITH THE SAME AND METHOD OF OCULAR SURGERY

TECHNICAL FIELD

The present invention relates to a decompression-compensating instrument for use in intraocular surgery for treating cataracts, etc., wherein a perfusate is supplied to an affected part in the eye via a supply channel at a predetermined pressure, and the perfusate is aspirated via an aspiration channel together with the tissues in the affected part that are to be removed, the decompression-compensating instrument supplying the perfusate into the affected part when the internal pressure of the affected part is excessively lowered; an instrument for use in ocular surgery provided with the same; and a method of ocular surgery.

BACKGROUND ART

In recent years, eye diseases such as cataracts are often treated with an operation that replaces the affected crystalline lens in the eye with an intraocular lens (an artificial crystalline lens). Phacoemulsification and aspiration (PEA) is widely employed in such a surgical operation wherein the affected crystalline lens is pulverized and emulsified using ultrasonic vibration and then the pulverized part is aspirated. In this surgical operation, an apparatus such as, for example, that shown in FIG. 16 is used. This apparatus is constructed so that a supply tube 51 for introducing a perfusate into the anterior chamber S of the affected part of the eye is connected to an ultrasonic handpiece 53, which is an apparatus for use in PEA (hereafter, this apparatus may be simply called a "handpiece"). The handpiece 53 is provided with an inlet channel 54 (see FIG. 17) for introducing the perfusate to the affected part, and the supply tube 51 is connected to the rear end of the inlet channel 54. A perfusate bottle 55 holding the perfusate is connected to the supply tube 51. By placing the perfusate bottle 55 at a predetermined height, it is possible to supply the perfusate into the anterior chamber S by allowing it to drip freely by its own weight from the perfusate bottle 55.

In a surgical operation, a crystalline lens P is pulverized and emulsified by ultrasonic vibration while supplying the perfusate into the anterior chamber S. The emulsified crystalline lens is aspirated and discharged together with the perfusate by an aspiration pump 59 that is connected to an aspiration channel 57 (see FIG. 17) provided in the handpiece 53. The anterior chamber is kept stable by the stable balance between the inflow rate (inflow pressure) of the perfusate and the aspiration rate (aspiration pressure).

However, this apparatus has the following problems. Generally, the PEA conducted in a cataract operation is performed in such a manner that fragments of the lens nucleus P1 are drawn to the tip entrance as shown in FIG. 17, and the fragments are then emulsified and aspirated by ultrasonic vibration using a dribble effect. At this time, the tip entrance is blocked by the lens nucleus P1, and the inflow of the perfusate is stopped while the tip entrance is blocked. When aspiration is further conducted under this condition, negative pressure builds up in the aspiration channel 57 and the lens nucleus P1 is aspirated. The obstructive state of the aspiration channel 57 is thereby cleared, and at that moment, the instantaneous aspiration rate rapidly increases and the inside of the anterior chamber S becomes decompressed.

However, because it is impossible to control the supply of the perfusate instantaneously to cope with this decompressed state, a condition continues wherein the amount of perfusate aspirated into the aspiration channel 57 is greater than that supplied from the supply tube 51. This adversely affects the balance between the inflow rate (pressure) and aspiration rate (pressure) of the perfusate, and the anterior chamber becomes unstable. As a result, the decompressed condition in the anterior chamber S continues (hereunder, this is called a "surge") until the inflow of the perfusate that was previously stopped reaches a certain rate and the inflow pressure and aspiration pressure eventually achieve a state of equilibrium. This causes a so-called microcollapse in which the internal capacity of the eyeball and anterior chamber decreases, which may cause further destruction of the posterior chamber and damage to the corneal endothelium.

Conventionally, operators coped with this problem by suitably selecting the amount of ultrasonic waves and aspiration amount based on their actual experience and/or practice. Therefore, it was not easy for inexperienced surgeons to cope with this problem.

To reduce such a surge, WO97/37700, for example, discloses an apparatus for detecting the blockage in an aspiration line using a vacuum sensor provided in the aspiration line. This apparatus is designed so that, when a blockage in the aspiration line is detected, the rate of the perfusate flowing into the eye is changed by controlling the speed of the peristaltic pump with a computer. U.S. Published Application No. 2002/0019607 and Japanese Unexamined Patent Publication No. 2002-153499 disclose an apparatus comprising an irrigation reservoir for storing irrigation fluid, a range, an irrigation pressure sensor and a pressure controller provided at a point midway along the irrigation line. This apparatus prevents the internal pressure of the anterior chamber from dropping below a specified value by using the controller to operate the irrigation reservoir in such a manner that an irrigation fluid is forcibly supplied to an irrigation supply channel when the irrigation pressure exceeds an appropriate range.

However, because the surge occurs instantaneously for a short time of less than about 0.2 second, it is difficult in practical terms to suppress the surge without any time lag using these apparatuses.

U.S. Pat. No. 6,042,586 discloses an apparatus which is connected to an irrigation supply line for preventing a cornea from collapsing. This apparatus comprises a main body provided with a dome-shaped head having a through bore and a thin latex film having a fixed periphery attached to this head so as to block this through bore. Because the thin film is elastic, when the irrigation flows to the thin film side via the through bore, the thin film stretches so as to form a chamber between the film and the head.

EP Patent No. 0180317 and U.S. Pat. No. 4,841,984 disclose that a pressure chamber is connected in series or in parallel to an irrigation fluid tube. This pressure chamber is formed into a spherical shape having an elastic surface. They state that it is preferable that the sphere have a diameter of 4 to 8 cm and be disposed 6 to 10 cm from a needle tip. It is also disclosed that by filling the chamber with air or other gas from the beginning, the time for responding to the change in intraocular pressure can be shortened.

However, because in intraocular operations such as cataract surgery, very precise and delicate manipulation is required, if the chamber is located at a position 6 to 10 cm from the tip of the handpiece as mentioned above, the motion of the hands operating the handpiece is restricted and this interferes with the surgery. During the surgery, the handpiece may be rotated around its axis or pivoted around its tip to aspirate the nucleus, and when the handpiece moves, the chamber also moves with it. This may cause the airspace in the chamber to move toward the irrigation inflow hole (the portion connected to the irrigation inflow line). This not only prevents the irrigation fluid from being promptly supplied but also raises the possibility that air may flow into the eyeball, which may cause additional damage to the intraocular tissues that is different from that caused by the surge.

Furthermore, because it is difficult to mount the chamber near the handpiece, depending on the motion of the chamber, the irrigation supply tube that composes the irrigation supply line may be strongly twisted. This would prevent the irrigation fluid from being supplied to the eye and may cause the anterior chamber to collapse due to strong aspiration pressure and lead to a serious accident.

Japanese Unexamined Patent Publication No. 1998-43229 discloses an apparatus comprising a perfusate reservoir means which stores perfusate, and has an air chamber disposed in the pathway of a perfusion tube. However, this publication discloses that it is preferable that the perfusate reservoir be located near the handpiece, and this may cause the same kind of problem as described above for the chamber.

The publication also discloses the steps of supplying the perfusate into the perfusate reservoir means as follows: A piston provided in the perfusate reservoir means is pressed down to exhaust the air in the perfusate reservoir means via an air inlet hole in an infusion tube that is connected to the perfusion tube. When the piston returns to its original position due to hysteresis, perfusate in an amount equal to the capacity occupied by the transferred piston is aspirated into the perfusate reservoir means from the perfusion bottle. The present inventor and associates produced the same apparatus as the above-mentioned perfusate reservoir, and examined the effect. When they tried to discharge the air in the perfusate reservoir by pressing the piston, not only could the air not be discharged from the air inlet hole but the piston could not even be pushed down. Therefore, the present inventor and associates verified that a perfusate cannot be supplied using the above-described perfusate reservoir. It is assumed that this is because the air inlet hole of commonly used infusion tubes is communicably connected to the perfusion bottle to keep the pressure in the perfusion bottle stable, and the perfusate reservoir is structured so as to prevent the perfusate and/or air from leaking outside via the air inlet hole.

The present inventor proposed an intraocular surgical apparatus comprising a decompression-compensating instrument as disclosed in Japanese Unexamined Patent Publication No. 2001-170102 (corresponding U.S. patent Publication No. 2002/0095113A1). As shown in FIG. 18, this intraocular surgical apparatus comprises a tube 63 (whose inner diameter is the same as that of a supply tube 51) having a plug 61 on one end, the tube 63 serving as a storage member for the decompression-compensating instrument and being connected to the supply tube 51 at a midpoint thereof. This intraocular surgical apparatus is used in the following manner. The end of the handpiece is first inserted in the anterior chamber S to start a the surgery. At this moment, the internal pressure (or capacity) of the anterior chamber S, which is the intraocular pressure, is kept stable by the balance between the inflow rate (inflow pressure) of the perfusate and the aspiration rate (aspiration pressure). During the surgery, when the balance between the inflow rate (inflow pressure) of the perfusate flowing into the anterior chamber S and the aspiration rate (aspiration pressure) is stably maintained and the emulsified crystalline lens is smoothly discharged, the air in the tube 63 is compressed between A-B as shown in FIG. 18. When the aspiration channel 57 is blocked by fragments of the lens nucleus, the inflow pressure of the perfusate affects the anterior chamber S. The air between A-B is further compressed so as to have the same pressure as the anterior chamber S, and the air capacity is reduced to that between A-C as shown in FIG. 19. In other words, the perfusate flows in the tube 63 in the amount equivalent to the capacity between B-C, which corresponds to the capacity of the air compressed. Although the aspiration pump 59 keeps aspirating the perfusate, the amount of perfusate in the aspiration channel gradually decreases because of the blockage thereof, resulting in a rapid increase of the negative pressure in the aspiration channel. When the fragment of the lens nucleus that was blocking the aspiration channel 57 is aspirated, the negative pressure is rapidly transferred to the anterior chamber S and then to the tube 63. Following the rapid decrease of the pressure in the anterior chamber S, the air between A-C in the tube 63 expands to the area between A-D as shown in FIG. 20. This pushes the perfusate stored between C-D out, wherein it flows to the anterior chamber S. This alleviates the rapid decrease of the pressure in the anterior chamber S and the stable balance between the inflow rate of the perfusate and the aspiration rate is maintained, preventing microcollapse.

Subsequently, the present inventor conducted extensive research to improve the above invention and found that when a tube serving as a storage member of a decompression-compensating instrument is disposed on the handpiece, from the moment that the surge occurs until it returns to a normal perfusion condition, the perfusate does not flow to the anterior chamber at a stable rate depending on the capacity or inner diameter of the tube. As described above, if the surge occurs when the tube is disposed thereon, the perfusate flows from the tube into the anterior chamber in accordance with the decompressed condition of the anterior chamber, but thereafter the perfusate flows to the anterior chamber via the supply tube as usual. However, depending on the capacity of the tube, etc., when the inflow of the perfusate changes from the tube to the supply tube, the inflow does not switch smoothly. When such a phenomenon occurs, the inflow of the perfusate to the anterior chamber sometimes cannot adequately cope with the surge and the decrease of the pressure in the anterior chamber may not be reliably alleviated.

An object of the present invention therefore is to provide a decompression-compensating instrument that reliably prevents the affected part in the eye from being rapidly decompressed during surgery for treatment of cataracts, etc., a surgical apparatus equipped with this instrument for use in intraocular surgery, and a method for conducting surgery using the same.

DISCLOSURE OF THE INVENTION

The present inventor conducted extensive research to achieve the above object and found that the decrease in the pressure in the anterior chamber can be reliably reduced by connecting a decompression-compensating instrument comprising a storage member having a predetermined capacity to a point midway along the supply channel that supplies the perfusate to the affected part.

In other words, the present invention relates to a decompression-compensating instrument which is used in intraocular surgery, wherein a perfusate is fed into an affected part of the eye via a supply channel by a predetermined pressure and aspirated via an aspiration channel together with the affected tissues that are to be removed, wherein the decompression-compensating instrument supplies the perfusate into the affected part when the internal pressure of the affected part is excessively lowered, has a construction that is connectable to a point midway along the supply channel, and comprises a storage member that forms a chamber that is closable except for an opening from which the perfusate that is to be supplied to the supply channel flows, and the capacity of the storage member is 7 cm$^3$ to 22 cm$^3$.

According to the decompression-compensating instrument of the present invention, because the storage member having a capacity of 7 cm$^3$ to 22 cm$^3$ is connected to a point midway along the supply channel that supplies the perfusate to the affected part of the eye, the perfusate is supplied from the storage member when the surge occurs, and therefore it is possible to prevent a rapid decrease in the inflow rate (pressure) caused by a loss of balance between the inflow rate (pressure) of the perfusate and the aspiration rate (pressure). Accordingly, it is possible to reliably prevent the decrease of the pressure in the affected part of the eye when the surge occurs.

It is preferable that the storage member be composed of a tube having the opening at one end.

It is also preferable that when the inner diameter of the tube is 4 mm, the length of the tube be not less than about 60 cm and not more than about 175 cm, and when the inner diameter of the tube is 3.5 mm, the length thereof be not less than about 72 cm and not more than about 230 cm.

It is further preferable that the inner diameter of the tube be larger than the inner diameter of the supply channel at the point upstream from the connection to the tube. It is particularly preferable that the inner diameter of the tube be not less than 1.1 times and not more than 1.7 times larger than the inner diameter of the supply channel at the point upstream from the connected portion.

When a commonly used perfusate supply tube (with an inner diameter of about 3 mm) is used, the inner diameter of the tube is not smaller than 3.3 mm and not greater than 5.1 mm, and therefore it is preferable that the inner diameter of the tube be not smaller than 3.5 mm and not greater than 5.0 mm.

An intraocular surgical apparatus of the present invention can be held in the operator's hand, the apparatus comprising an inlet channel for supplying the perfusate into the intraocular affected part, a compensating instrument connected to a point midway along the inlet channel for use in intraocular surgery, a pulverizing member for pulverizing a predetermined affected tissue in the eye, and an aspiration channel for aspirating the affected tissue together with the perfusate.

Because this intraocular surgical apparatus is provided with the above-described decompression-compensating instrument, it is possible to alleviate the decrease in the pressure of the intraocular affected part when a surge occurs during surgery for treatment of cataracts, etc. Furthermore, because the surgical instrument is integrated with the decompression-compensating instrument, it is easier to use during surgery.

The above-described storage member of the decompression-compensating instrument used in intraocular surgery can be mounted on the main body of an intraocular surgical apparatus that includes a pulverizing member. In this case, the storage member may be disposed on the rear end of the main body. Alternatively, when the storage member is composed of a tube, the tube may be wound around the main body.

A method for intraocular surgery of the present invention is as follows. While supplying the perfusate into the affected part of the eye via a supply channel using a predetermined pressure, the perfusate is aspirated though an aspiration channel together with the affected tissue that is to be removed, the method comprising the steps of:

preparing a decompression-compensating instrument for use in intraocular surgery, the decompression-compensating instrument comprising a storage member having a chamber that is closed except for an opening, the capacity of the storage member being not less than 7 cm$^3$ and not greater than 22 cm$^3$;

making the storage member and the supply channel communicate with each other through the opening by connecting the decompression-compensating instrument to a point midway along the supply channel with air accommodated in the storage member;

supplying the perfusate to the supply channel, flowing the perfusate to the storage member via the supply tube, and containing the perfusate in the storage member under the affect of the air; and supplying the perfusate into the affected part of the eye while aspirating the affected part from the eye together with the perfusate.

BEST MODE FOR CARRYING OUT THE INVENTION

An embodiment of a decompression-compensating instrument of the present invention used in intraocular surgery and an intraocular surgical instrument using the same are explained below with reference to the drawings.

1. Decompression-Compensating Instrument

Figure 1:
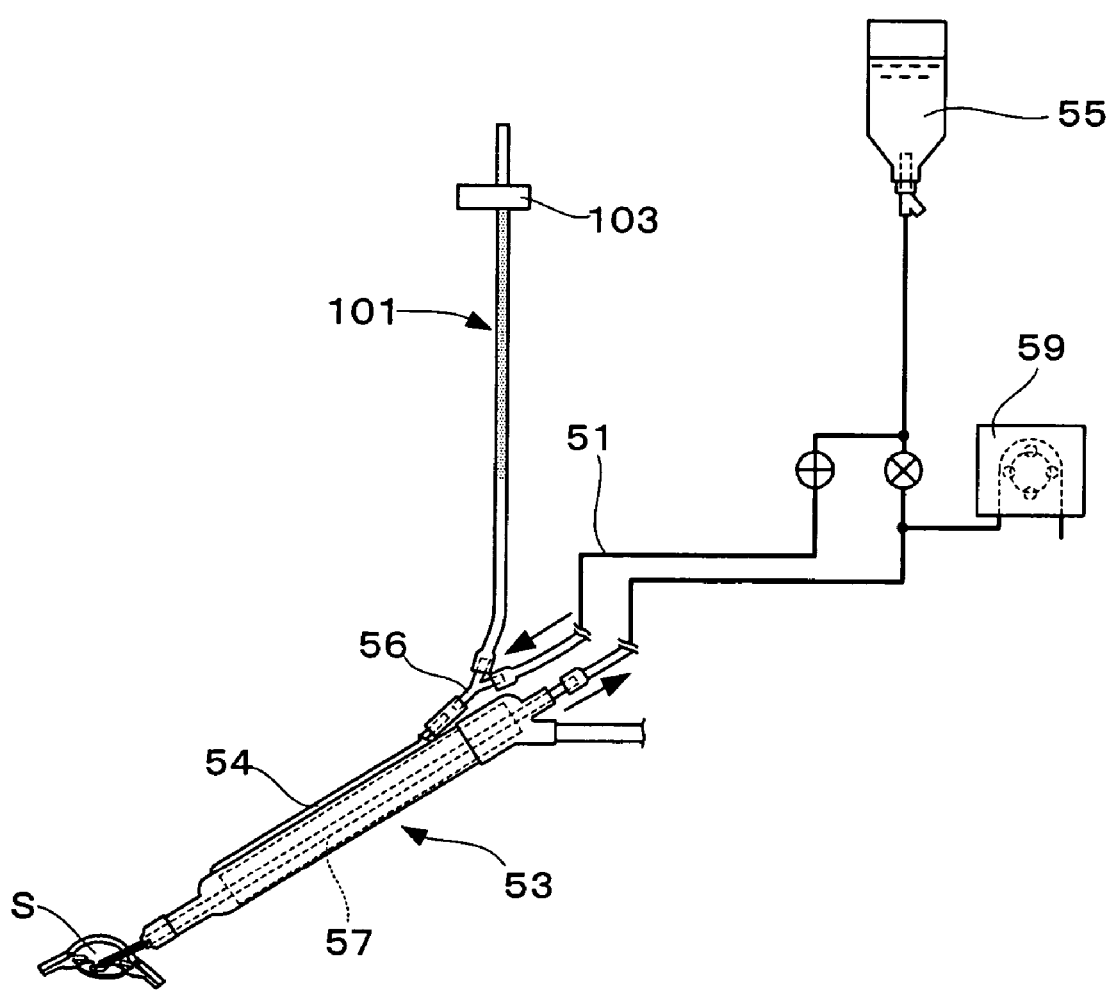
FIG. 1 illustrates an example of an apparatus comprising a decompression-compensating instrument of the present invention.
Figure 18:
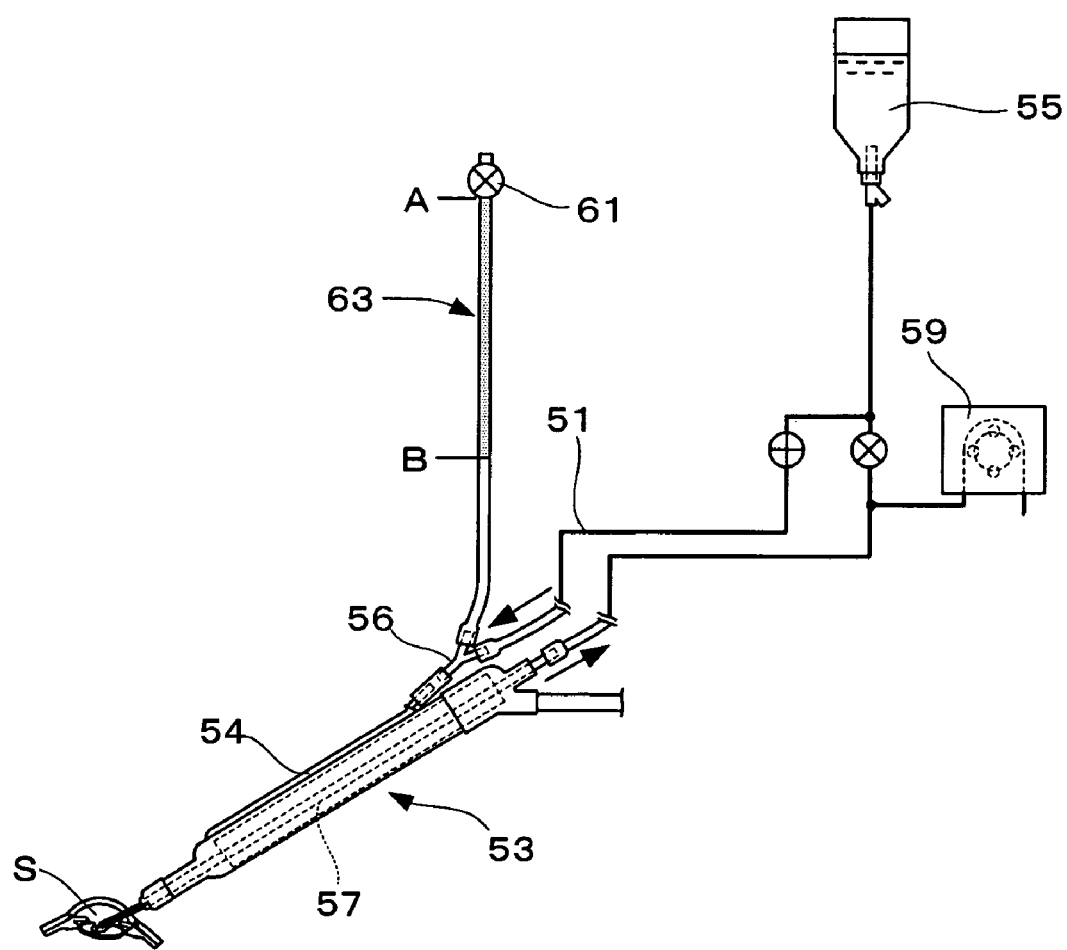
FIG. 18 illustrates a surgical apparatus proposed by the present inventor.
Figure 19:
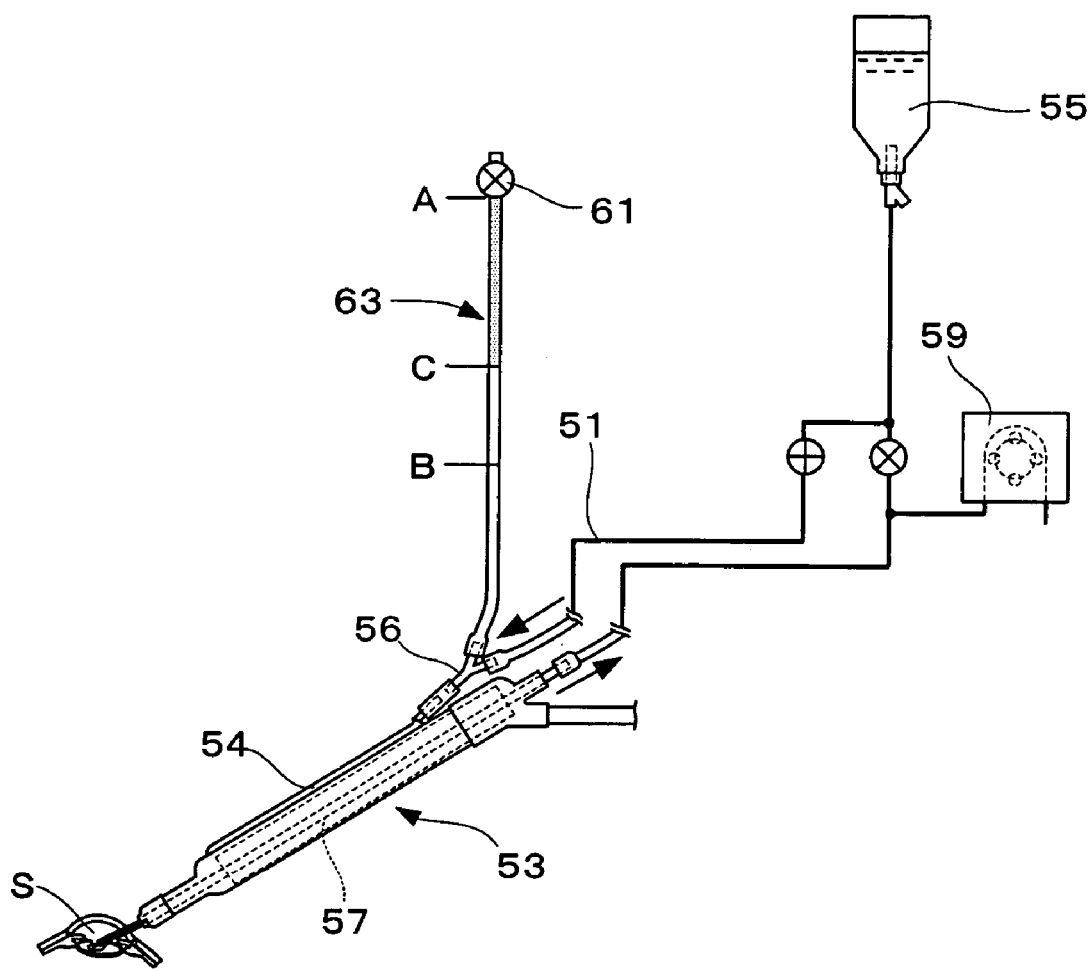
FIG. 19 illustrates a surgical apparatus proposed by the present inventor.
Figure 20:
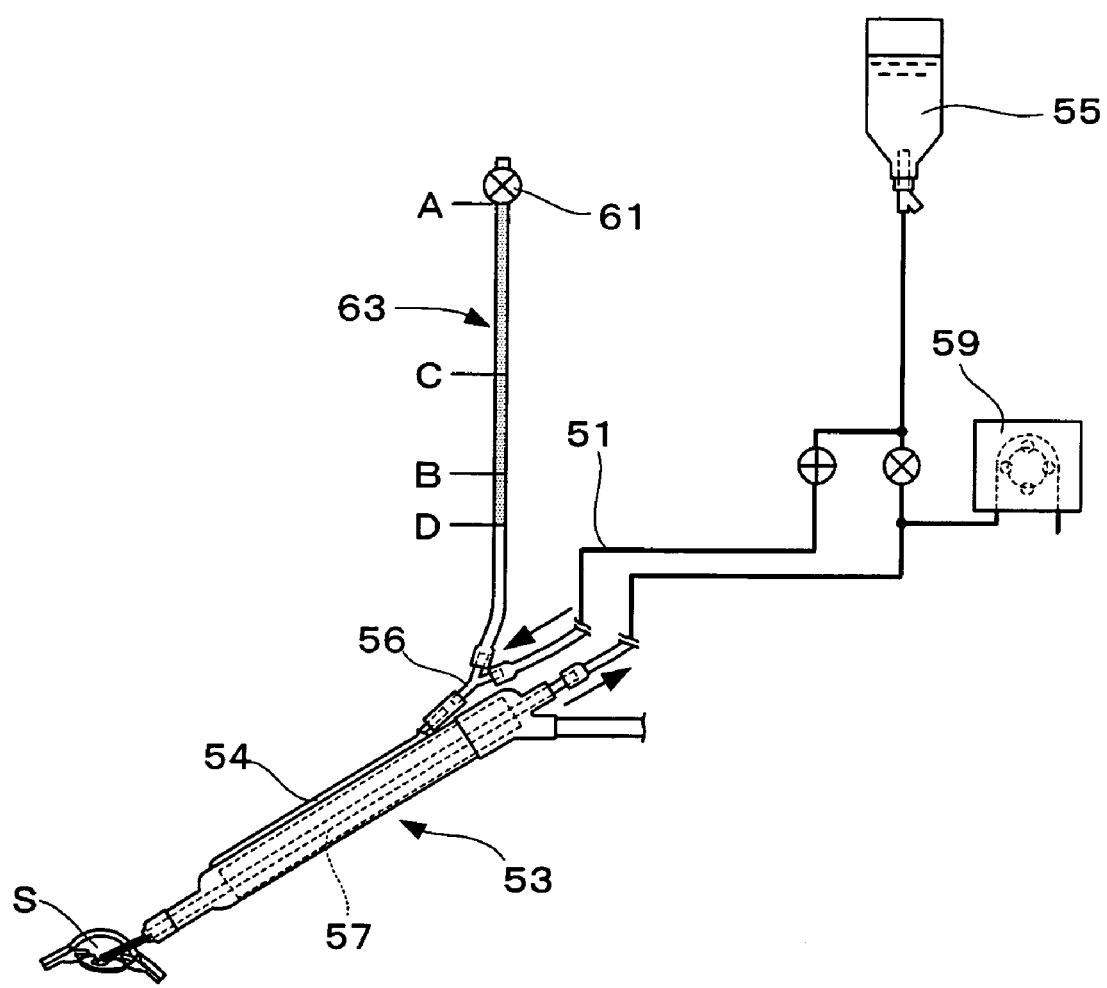
FIG. 20 illustrates a surgical apparatus proposed by the present inventor.

A decompression-compensating instrument of the present embodiment is provided with a tube (storage member) formed of silicon, etc., and is connectable to a handpiece as shown, for example, in FIG. 1. This handpiece is the same as a conventional one, as shown in FIG. 18, and therefore the same reference numbers are used for the same constituent components thereof and a detailed explanation is omitted. The opening at one end of a tube 101 can be connected to a joint tube 56 attached to the rear end of an inlet channel (supply channel) 54 of a handpiece 53. A perfusate bottle 55 is connected to the joint tube 56 via a supply tube (supply channel) 51. The other end of the tube 101 is blocked with a clamp 103, and the perfusate can flow in the tube 101. The present inventor designed the tube to have a capacity of not less than 7 $cm^3$ and not greater than 22 $cm^3$ to cope with a decrease in the pressure in the anterior chamber when a surge occurs.

The reason for this is as follows: The elevation of the perfusate bottle 55 is fixed, so the pressure of the air compressed in the tube 101 is the same regardless of the length of the tube 101. Therefore, when a surge occurs, perfusate in the tube 101 is pushed out at a constant pressure. However, if the tube 101 is long, the amount of perfusate stored in the tube 101 is large, whereas if the tube is short, the amount is small. Though the initial speed of the perfusate being pushed out is the same, when the amount of perfusate is small, the amount being pushed out is less. Therefore, the perfusate is pumped out by the compressed air in the tube and the speed of the perfusate does not decrease very much from the initial speed. In contrast, it is assumed that if the amount of perfusate is large, the amount being pushed out is also large, so the speed of the pumped out perfusate gradually decreases from the initial speed.

As described above, when the amount of perfusate stored in the tube 101 is small and the decrease from the initial speed of perfusate being pumped out of the tube 101 is small, the supply of perfusate from the tube 101 takes priority over the supply of perfusate from the supply tube 51 which is suppressed. In this case, supply of perfusate from the supply tube 51 starts from a condition where the flow of perfusate from the supply tube 51 is substantially stopped, after the supply from the tube 101 has been completed. Therefore, the channels for supplying the perfusate are not exchanged smoothly.

When the channels cannot be smoothly exchanged as described above, the flow rate of the perfusate fed into the anterior chamber may rapidly decrease (i.e., approach a rate of 0) from the time that the inflow of the perfusate from the tube 101 is completed until a normal perfusion condition resumes. When this kind of phenomenon occurs, a pressure decrease in the anterior chamber cannot be reliably prevented since the amount of perfusate inflow momentarily decreases.

In contrast, when the amount of perfusate stored in the tube 101 is large, the inflow rate of the perfusate from the tube 101 to the anterior chamber gradually decreases, so the amount of perfusate supplied from the supply tube 51 is not rapidly suppressed. Therefore, as the flow rate of the perfusate from the tube 101 decreases, the perfusate also gradually flows into the anterior chamber from the supply tube 51. As a result, the inflow channels of the perfusate can be exchanged smoothly, and this prevents a decrease in the perfusate flow rate into the anterior chamber.

The present inventor found that when the capacity of the tube is not less than 7 $cm^3$, the amount of perfusate flowing into the anterior chamber does not greatly decrease. From this point of view, the capacity of the tube is preferably not less than 8 $cm^3$, more preferably not less than 9 $cm^3$, still more preferably not less than 10 $cm^3$, and most preferably not less than 12.5 $cm^3$.

Cataract surgery comprises mainly the following four steps: (1) discission of the anterior capsular, (2) phacoemulsification and aspiration of the crystalline lens, (3) aspiration of the cortex, and (4) insertion of an intraocular lens. Because a different handpiece is used for each step (for example, an ultrasonic handpiece is used for phacoemulsifying and aspirating the crystalline lens, and an I/A (irrigation and aspiration) handpiece is used for aspirating the cortex), when moving to the next step, it is necessary to remove the handpiece from the anterior chamber. At this time, because the inlet channel 54 in the handpiece is opened and has no resistance, all of the perfusate in the tube 101 is released to the surgical site outside the eyeball. In this case, when the capacity of the tube 101 is unduly large, the amount of perfusate left in the tube is large and the amount of liquid supplied to the surgical site is also large, so it takes a long time to discharge it. This adversely affects the efficiency of the cataract surgery, which needs to be conducted in a short time. Furthermore, it is not preferable for the amount of perfusate supplied to the surgical site to be large, because this may cause contamination in the surgical site. Taking those points into consideration, the capacity of the tube 101 is preferably not more than 22 $cm^3$, more preferably not more than 20 $cm^3$, still more preferably not more than 17.5 $cm^3$, and most preferably not more than 15 $cm^3$. When the inner diameter of the tube is 4 mm, this corresponds to the length of the tube being about 175 cm, about 159 cm, about 139 cm or about 119 cm; and when the inner diameter of the tube is 3.5 mm, it corresponds to the length of the tube being about 229 cm, about 208 cm, about 182 cm or about 156 cm.

The present inventor also found that the inner diameter of the tube 101 that serves as a decompression-compensating instrument is preferably 1.1 to 1.7 and more preferably 1.2 to 1.4 times as large as the perfusate supply tube 51 (the portion upstream from the tube in the pathway of the perfusate). This will be explained in detail under the heading of Examples. These values are obtained using the kind of perfusate inlet tube (with an inner diameter of about 3 mm) that is commonly used in intraocular surgery as the perfusate supply tube 51. Examples of commonly used perfusate inlet tubes include the disposable tube (with an inner diameter of about 3 mm) included in the AMO MAXPA™ Disposable Tubing Set OM20, and the disposable silicon tube (with an inner diameter of about 3 mm) included in the AMO™ SOVEREIGN Pack Disposable Tubing Set REF (Part No.: OPO50). It is also possible to use the Maxvac aspiration tube ?(manufactured by Alcon), the Phaco-Emulsification System CV-24000 disposable cassette disk (manufactured by Nidek Co., Ltd.), etc.

Furthermore, when the inner diameter of the tube 101 is in the range from 1.1 to 1.7 times as large as the perfusate supply tube 51, even if the tube 101 rotates in accordance with the movement of the handpiece or one of the ends blocked with the clamp 103 hangs down, the air layer stays on the clamp 103 side without any switching of the perfusate stored in the tube 101 and the air of an air layer. Because the perfusate stored in the tube 101 and that which is supplied from the supply tube 51 are not divided by an air layer, this arrangement can reliably prevent air from flowing into the eye as is the case when a conventional spherical chamber, etc., is used and the perfusate layer and the air layer switch places.

Furthermore, because the tube 101 has a long, thin shape, similar to that of the supply tube 51, the handpiece can be operated without being concerned about the movement of the tube 101 during surgery and the above-described effects can be achieved to cope with surges. Furthermore, the tube can easily be held in parallel to the perfusate supply channel 51, for example, by holding the tube with adhesive tape, etc., so that the tube is united with the perfusate supply channel 51. This allows the operator to handle the handpiece in the same manner as when no tube is attached. Therefore it is preferable that the parts in the joint tube 56 to which the supply channel 51 is connected and to which the tube 101 is connected be formed substantially parallel to each other.

From the viewpoint of frictional resistance, it is preferable to use a tube having an inner diameter larger than that of the supply tube 51. This is because when a surge occurs, the perfusate must start flowing from the tube 101 before it flows from the supply tube 51 to cope with the decompressed condition as soon as possible. Therefore, it is preferable that the inner diameter of the tube 101 is at least larger than that of the supply tube 51.

Figure 2:
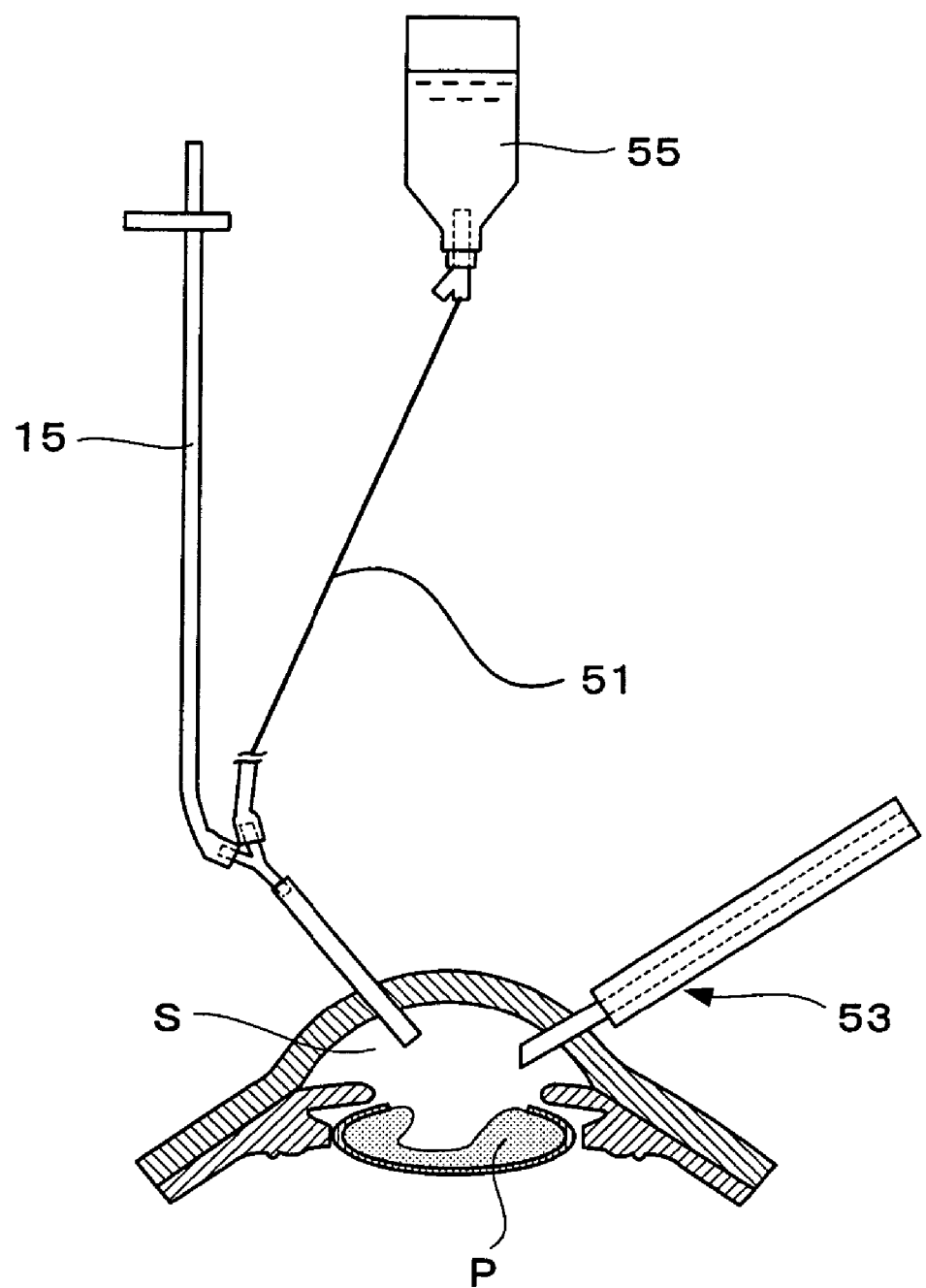
FIG. 2 illustrates another embodiment of an apparatus comprising a decompression-compensating instrument of the present invention.

In the present embodiment, the handpiece 53 is equipped with a tube that serves as a storage member of a decompression-compensating instrument; however, the present invention is not limited to this and may be structured, for example, as shown in FIG. 2. In other words, it is also possible to supply the perfusate directly to the anterior chamber S via the supply tube 51 without passing through the handpiece 53, and a tube 15 that serves as a storage member of the decompression-compensating instrument is connected to a point midway along the supply tube 51, as shown in FIG. 2. This structure also prevents surges because perfusate is supplied to the anterior chamber S in the same manner as when the perfusate is supplied from the handpiece 53.

To close the ends of the tubes 101 and 15, various substances other than the clamp 103 can also be used. It is also possible to seal the end of the tube by inserting a substance of the same or different material as/from the tube 101 or by melting the end of the tube 101.

Flexible and elastic materials having chemical resistance and heat resistance can be used as materials for the tubes 101 and 15. Specific examples include natural rubber, isoprene rubber, styrene rubber, butyl rubber, butadiene rubber, ethylene-propylene rubber, nitrile rubber, chloroprene rubber, Hypalon®, urethane rubber, silicon rubber, epichlorohydrin rubber, etc., and silicon rubber is particularly preferable. Polypropylene tube, polyethylene tube, multi-W tubing, silicon tube, unitube, and Tygon® 3355L are suitably used as the tube.

2. Handpiece (Intraocular Surgical Apparatus)

Figure 3:
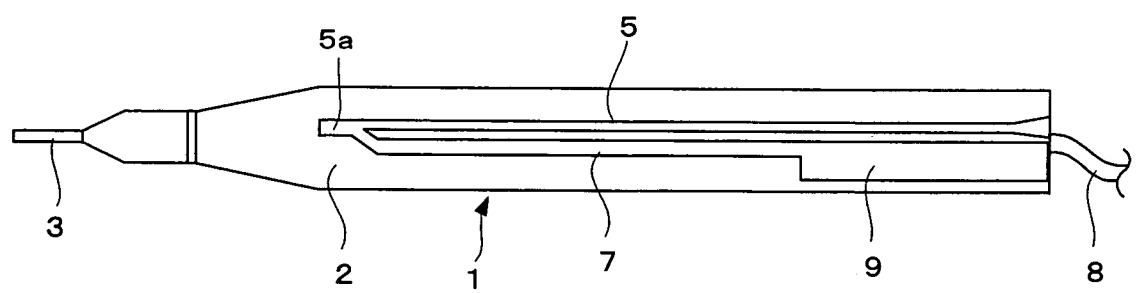
FIG. 3 illustrates an example of an intraocular surgical apparatus of the present invention.
Figure 3:
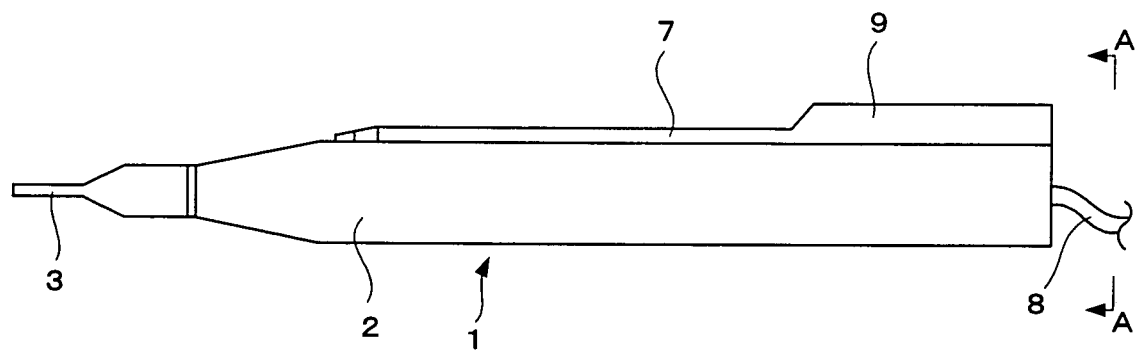
Figure 3:
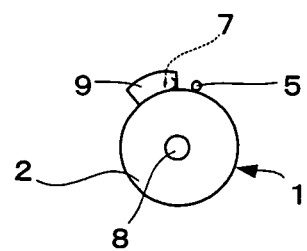

An embodiment of a handpiece using the above-explained decompression-compensating instrument of the present invention is explained below with reference to FIG. 3. FIG. 3(a) is a plan view of the handpiece of the present embodiment, FIG. 3(b) is a front view and FIG. 3(c) is a cross-sectional view taken along the line A-A.

As shown in this figure, this handpiece 1 comprises a tubular-shaped main body 2 that can be held with operator's hands, the main body incorporating an oscillator for generating ultrasonic vibration and a horn (not shown) for outputting ultrasonic vibration generated by the oscillator, wherein a tubular tip 3 for pulverizing and emulsifying the crystalline lens is provided on the end of the handpiece. The tubular tip 3 is connected to the horn and applies ultrasonic vibration to the crystalline lens subjected to surgical operation. The above-mentioned oscillator, horn and tubular tip 3 comprise the pulverizing member of the intraocular surgical apparatus of the present invention.

An inlet channel 5 for supplying perfusate to the affected part is connected to the end of the handpiece 1. This inlet channel 5 extends in the direction along the axis of the handpiece 1, the inlet channel 5 being incorporated in the handpiece 1 in the vicinity of the front end and exposed to the outside from the midstream. A supply tube for supplying perfusate from a perfusate bottle can be attached to the rear end portion of the inlet channel 5. A tube 7 that functions as a storage member of the decompression-compensating instrument is connected to a point midway along the exposed portion of the inlet channel 5 and extends parallel to the inlet channel 5. An extended portion 9 is provided in the rear portion of the tube 7 to increase the capacity of the tube. The extended portion 9 is formed into a rectangular shape as seen in a plan view and attached to the outer surface of the rear portion of the handpiece 1. An aspiration tube 8 is provided to the rear end portion of the handpiece 1 to aspirate the emulsified crystalline lens from the eye together with the perfusate. In the present embodiment, the tube 7 and the extended portion 9 compose the storage member of the decompression-compensating instrument of the present invention.

The dimensions of the tube 7 and the extended portion 9 are as described in the above embodiments. In other words, the inner diameter of the tube 7 is preferably 1.1 to 1.7 times and more preferably 1.2 to 1.4 times as large as the inlet channel 5 (in the portion upstream from the point connected to the tube). The total capacity of the tube 7 and the extended portion 9 is preferably not less than 7 cm$^3$ and not more than 22 cm$^3$; however, taking the dimensions of the handpiece into consideration, it is more preferable that the total capacity be not less than 7 cm$^3$ and not more than 15 cm$^3$. The larger the inner diameter of the pathway 5a extending from the junction between the inlet channel 5 and the tube 7 to the tubular tip, to lower resistance in the pathway, the more preferable. It is preferable that the inner diameter be at least larger than that of the tube 7.

As described above, because the tube 7 and the extended portion 9 serving as a storage member of the decompression-compensating instrument are united with the handpiece 1, the handpiece 1 of the present embodiment offers improved operability compared to a handpiece wherein a tube is attached to its outside.

Figure 4:
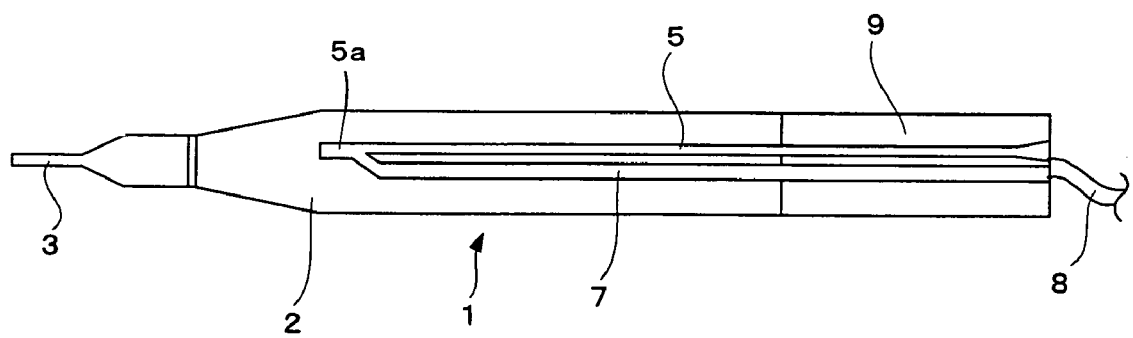
FIG. 4 illustrates another example of an intraocular surgical apparatus of the present invention.
Figure 4:
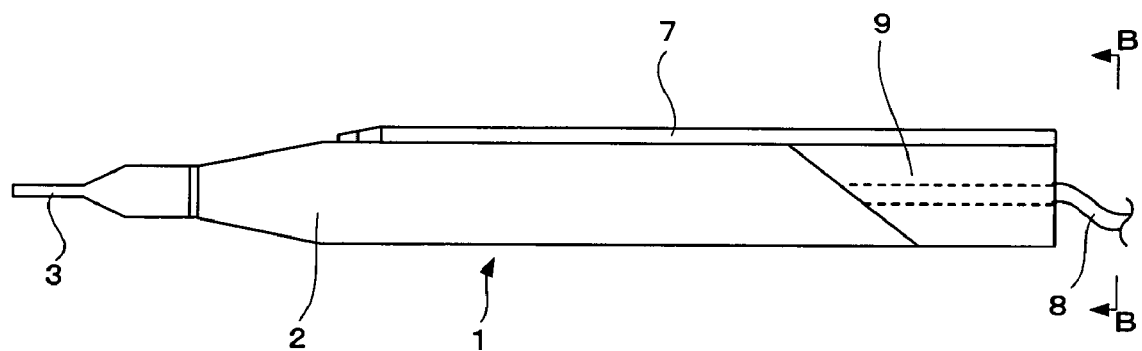
Figure 4:
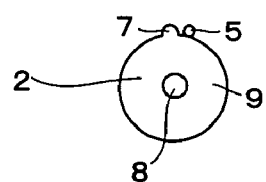

In the present embodiment, the handpiece 1 and the decompression-compensating instrument are united into one body; however, the present invention is not limited to this and, for example, it may have the following construction. As shown in FIG. 4, in this case, the extended portion 9 is attached to the rear end portion of the handpiece 1, the extended portion 9 having substantially the same outer diameter as the handpiece 1 and being formed into a doughnut shape that extends in the direction along the axis. The aspiration tube 8 is inserted into the hollow portion of the doughnut shape. This arrangement further improves the operability of the handpiece, because no protruding parts are formed around the outer surface of the handpiece 1.

Figure 5:
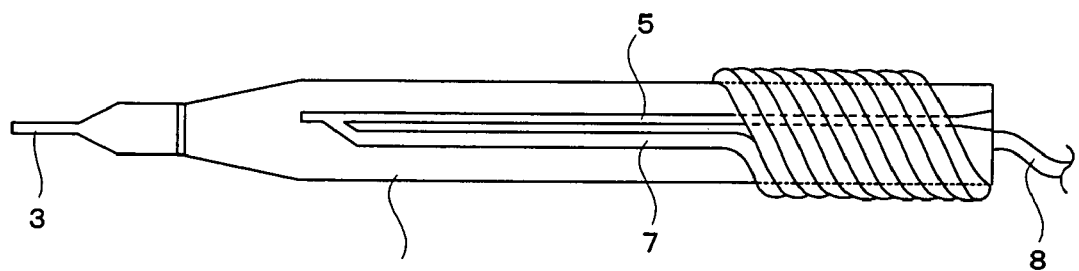
FIG. 5 illustrates still another example of an intraocular surgical apparatus of the present invention.
Figure 5:
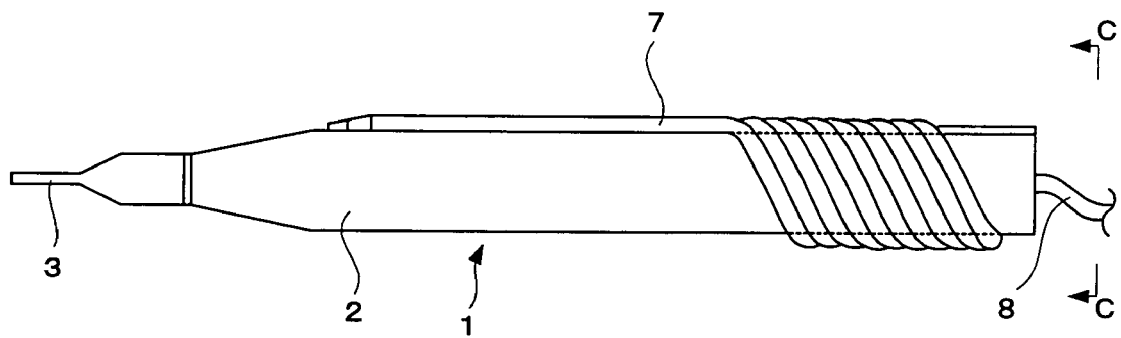
Figure 5:
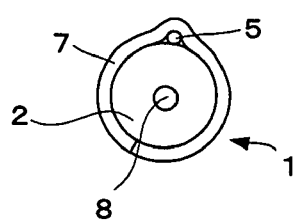

It is also possible to form the handpiece so as to have the following structure. In the embodiment shown in FIG. 5, a storage member of a decompression-compensating instrument is composed of a tube 7 without an extended portion, and the rear end portion of the tube 7 is wound around the main body 2 of the handpiece 1 to form a spiral shape. Because this arrangement does not require any additional components such as an extended portion, the capacity of the decompression-compensating instrument can be increased while saving space, thus miniaturizing the handpiece.

Note that other than the above-described structure, it is also possible to employ various constructions wherein a handpiece and a decompression-compensating instrument are united into one body. For example, if it is possible to form a space within the handpiece, the decompression-compensating instrument can be incorporated in the handpiece. It is also possible to form the storage member (a tube and an extended portion) of the decompression-compensating instrument having the above shape as a removable attachment, and attach it to the handpiece in a united manner when used.

Also, while it is not shown in the above examples, when a reclosable plug is provided on a portion of the decompression-compensating instrument of the handpiece, it is readily possible to easily drain the perfusate, clean the decompression-compensating instrument, etc., through the reclosable plug.

EXAMPLE

Figure 6:
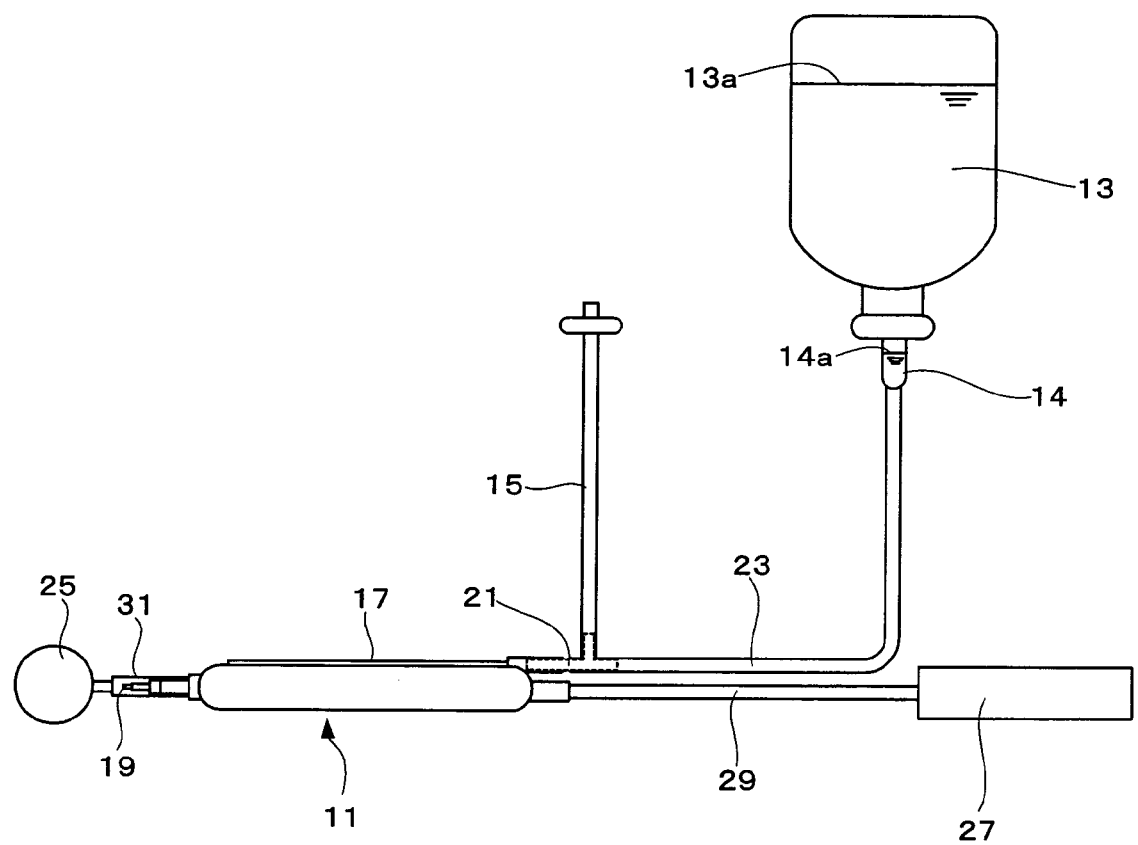
FIG. 6 illustrates an experimental apparatus for examining the relationship between the capacity of the tube that serves as a decompression-compensating instrument of the present invention and the amount of the perfusate that flows in the anterior chamber.

Hereunder, details of experiments conducted with the present invention are explained with reference to the drawings to further clarify the features of the present invention. FIG. 6 is a drawing schematically showing the structure of the experimental apparatus.

The capacity of the tube is explained below.

(a) Experiment 1

Focusing on the fact that the pressure in the anterior chamber during a surge changes in accordance with the pressure in the tube, experiments were conducted in which the capacity of the tube was varied. As shown in FIG. 6, the experimental apparatus used here comprises a handpiece 11, which is a phacoemulsification and aspiration device, and a perfusate bottle 13, which stores the perfusate, connected to the handpiece 11. The handpiece 11 is a piezoelectric, small phaco handpiece manufactured by AMO, which incorporates an inlet channel 17 for supplying the perfusate to the intraocular anterior chamber and an aspiration channel (not shown) through which the perfusate aspirated from the anterior chamber is sent. A cataract surgical device 27 is connected to the rear end portion of the aspiration channel via an aspiration tube 29. This surgical device 27 aspirates perfusate at a predetermined aspiration pressure. In this experiment, a "Series 2000 LEGACY ®" ultrasonic cataract surgical device (manufactured by Alcon Surgical) was used as the surgical device 27.

A tubular tip 19 that pulverizes and emulsifies the crystalline lens by receiving vibration from the ultrasonic vibrator is provided on top of the aspiration channel. The emulsified crystalline lens is aspirated with the perfusate from the tubular tip 19 via an aspiration channel. The perfusate used was a BSS Plus® manufactured by Alcon.

A joint tube 21 is attached to the rear end of the inlet channel 17 of the handpiece 11. A supply tube 23 for supplying the perfusate from the perfusate bottle 13 to the handpiece 11 and a tube 15 that functions as a decompression-compensating instrument are connected to the joint tube 21. A supply tube 23 having an inner diameter of 3 mm was used.

In this experiment, the handpiece was fixed to a base, and the tubular tip 19, which is the tip of the handpiece 11, was inserted into the mock anterior chamber 31. The mock anterior chamber 31 is a replica of the intraocular anterior chamber, which is the affected part. The perfusate bottle 13 was placed so that the fluid level 14a of a trap 14 that is attached to the perfusate supply tube 23 became the height of 70 cm from the top of the tubular tip 19.

When a surge occurs, it is difficult to measure the rate of the perfusate flowing out of the tube 15, and therefore the pressure in the mock anterior chamber 31 was measured in this experiment, and a pressure gauge 25 was provided to the mock anterior chamber 31. A silicon tube having an inner diameter of 4 mm, and length of 20 cm to 400 cm was used as the tube 15, which served as a decompression-compensating instrument.

Experiment 1-1

Figure 7:
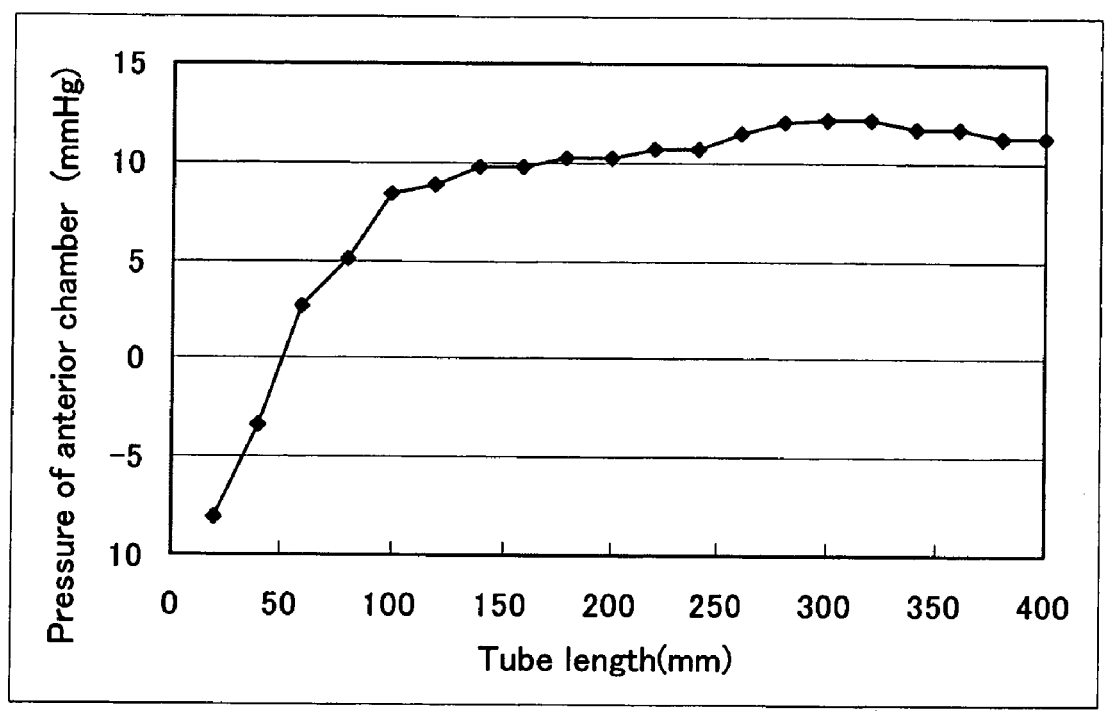
FIG. 7 is a graph showing the results of a test conducted using the experimental apparatus shown in FIG. 6.

The experiment method is described next. A perfusate was supplied to the perfusate tube 15 so as to compress the air in the tube 15. General perfusion was then conducted by setting the aspiration flow rate of the cataract surgical device 27 at 30 cc/min and the maximum aspiration pressure at 200 mmHg. After blocking the aspiration tube 29 with a clamp, the aspiration tube 29 was opened and the change in the pressure of the mock anterior chamber 31 was then measured. This change was defined as the change in pressure during the surge. FIG. 7 shows the results. In FIG. 7, the longitudinal axis indicates the pressure of the mock anterior chamber 31 during the surge, and the horizontal axis indicates the length of the tube 15. As is clear from FIG. 7, when the length of the tube was 60 cm or more, the pressure during the surge did not become negative, and when the length of the tube was 100 cm or more, the tube 15, which serves as a decompression-compensating instrument, operated in a stable manner. Converting tube length into capacity, when the length of the tube is 60 cm, the capacity thereof is 7.5 cm$^3$, and when the length is 100 cm, the capacity is 12.6 cm$^3$.

Experiment 1-2

The change in the pressure of the mock anterior chamber 31 attributable to the difference in the length of the tube was measured following the same manner as above using the same apparatus as in FIG. 6 except that no cataract surgical device 27 was provided. Experiment 1-1 was conducted with the aspiration flow rate of the cataract surgical device 27 set at 30 cc/min and the maximum aspiration pressure set at 200 mmHg; however, if the aspiration pressure changes, the pressure during the surge also changes. Therefore, the present inventor decided to consider a more preferable tube length by conducting an experiment under the condition that the mock anterior chamber would be unaffected by the aspiration pressure. The perfusate bottle 13 was disposed so that the fluid level 14a of the trap 14 that is attached to the perfusate supply tube 23 was at a height of 60 cm from the top of the tubular tip 19.

The perfusate was supplied by gravity via the supply tube 23, and was spontaneously discharged via an aspiration tube 29. The change in the pressure of the mock anterior chamber 31 was measured when the aspiration tube 29 was opened and closed using the clamp. The pressure of the mock anterior chamber 31 0.15 second after opening the closed aspiration tube 29 was defined as the pressure during the surge. This is because when the perfusate was aspirated using an aspiration pump by connecting the aspiration tube 29 to the cataract surgical device 27, the pressure of the mock anterior chamber 31 became minimum after about 0.15 second on average.

Figure 8:
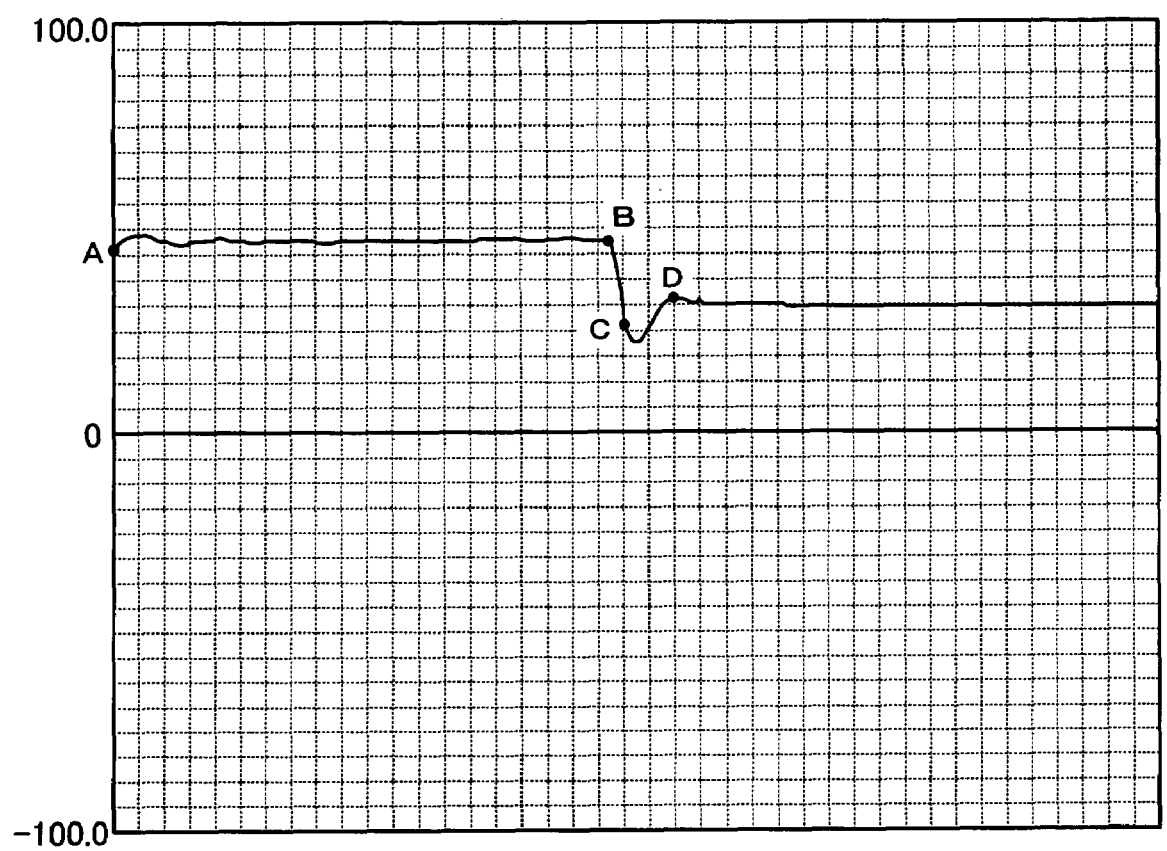
FIG. 8 is a graph showing the change in pressure in the tube when a tube having a length of 20 cm is used.
Figure 9:
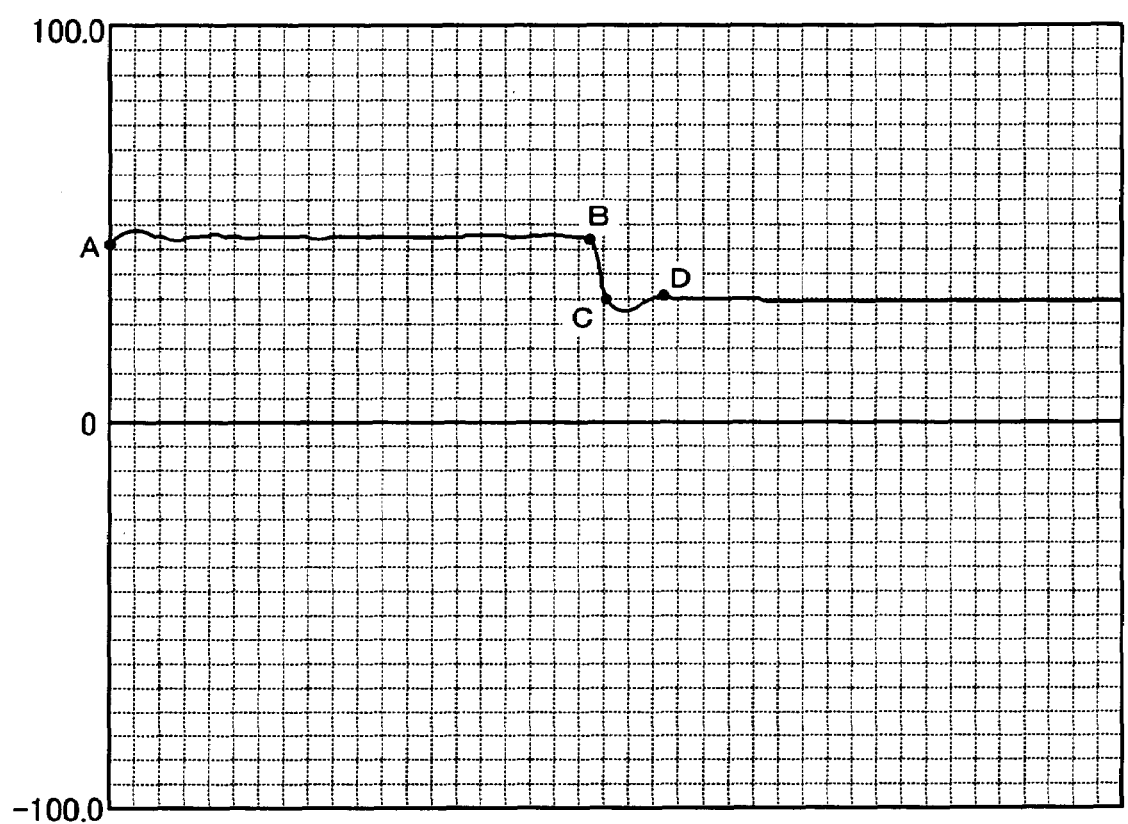
FIG. 9 is a graph showing the change in pressure in the tube when a tube having a length of 60 cm is used.
Figure 10:
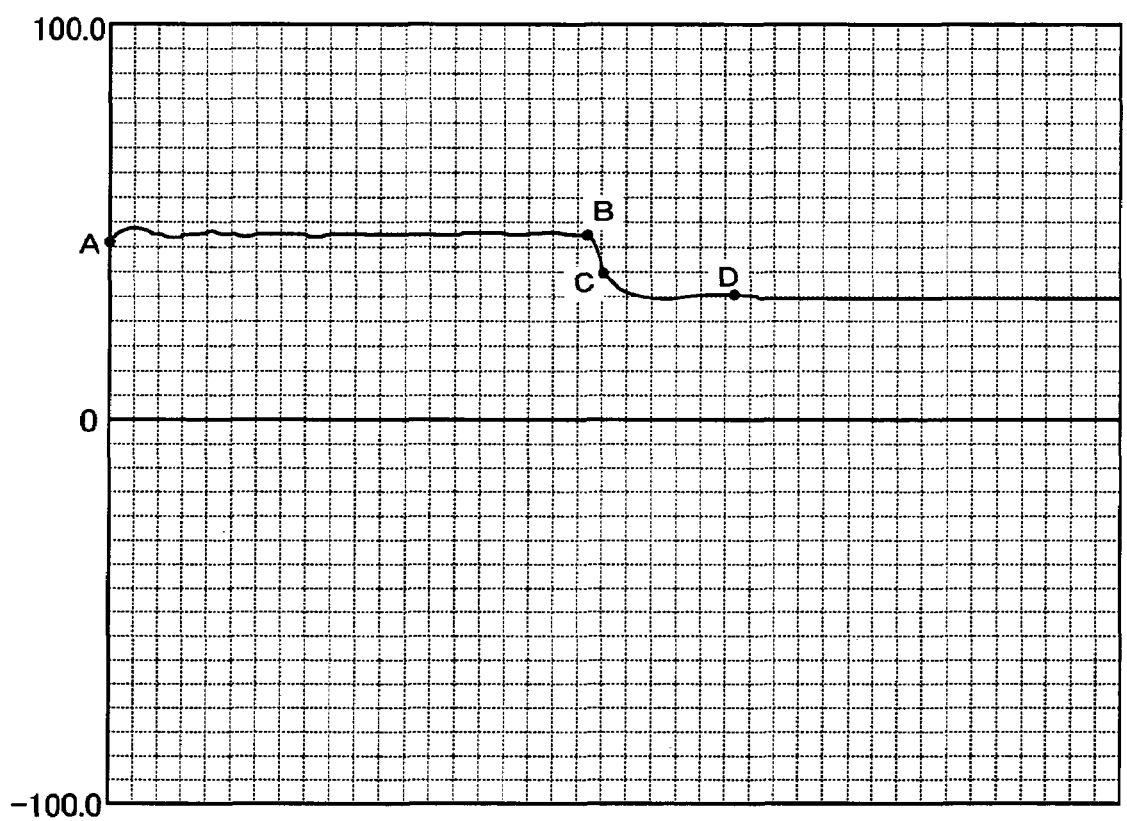
FIG. 10 is a graph showing the change in pressure in the tube when a tube having a length of 140 cm is used.

FIGS. 8 to 10 show the change in the pressure of the mock anterior chamber 31 when the length of the tube 15 was 20 cm, 60 cm or 140 cm. The pressure of the mock anterior chamber 31 when the aspiration tube 29 was blocked with the clamp was about 45 mmHg (between A-B). B indicates the point when the aspiration tube 29 was opened and C indicates 0.15 second after B. D indicates the point when it returned to normal perfusion. The pressure at C in FIGS. 8 to 10 was 26.6 mmHg, 30.4 mmHg, and 40.7 mmHg, respectively. The pressure in the tube 15 having a length of 20 cm or 60 cm was lower than that at normal perfusion (D) by 8.0 mmHg and 1.9 mmHg, respectively; however, the pressure of the tube 15 having a length of 140 cm was higher than that at normal perfusion (D) by 6.8 mmHg.

Figure 11:
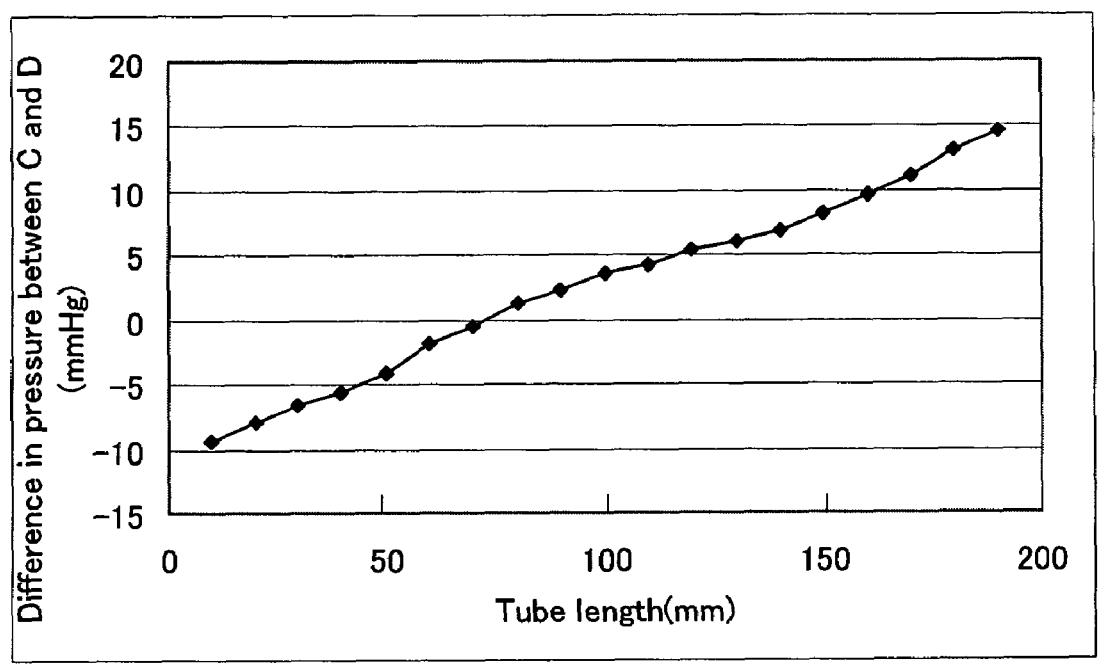
FIG. 11 is a graph showing the difference in pressure in a mock anterior chamber between during occurrences of a surge and normal perfusion, the difference being measured using another experimental apparatus for examining the relationship between capacity of the tube that serves as a decompression-compensating instrument of the present invention and the amount of the perfusate flowing in the anterior chamber.

FIG. 11 shows the difference in the change in pressure between C and D obtained in the experiment. The horizontal axis indicates the length of the tube. From FIG. 11, it is clear that when the length of the tube 15 is 80 cm or more, i.e., the capacity of the tube 15 is 10 cm³ or more, the pressure is no lower than that at normal perfusion, which is preferable.

As shown in these figures, the longer the tube 15, the less the pressure is reduced during the surge, and the pressure smoothly changes from when the aspiration tube is blocked until it returns to normal perfusion. This indicates that when the tube 15 is long, the reduction of the perfusate flow rate is less. In other words, the outflow of the perfusate from the tube 15 smoothly changes to that from the supply tube 23, and this prevents the flow rate of the perfusate being supplied to the anterior chamber from rapidly decreasing.

As described above, the longer the tube 15, the better. In particular, a tube of not less than 60 cm in length, wherein the pressure 0.15 second after the surge occurs is higher than that during the surge, is preferable and not less than 80 cm is more preferable. The capacities of tubes having an inner diameter of 4 mm and lengths of 60 cm and 100 cm are 7.54 cm³ and 12.5 cm³, respectively. Based on this, the capacity of the tube 15 is preferably not less than 7 cm³ and more preferably not less than 10.0 cm³.

As described above, from the viewpoint of surgical efficiency, the capacity of the tube is preferably not more than 22 cm³, more preferably not more then 20 cm³, still more preferably not more than 17.5 cm³, and most preferably not more than 15 cm³.

(b) Experiment 2

An experiment regarding the inner diameter of a tube used as a decompression-compensating instrument is explained below. The experimental apparatus used here is the same as that used in Experiment 1, i.e., that shown in FIG. 6, and therefore a detailed explanation is omitted.

A tube 15 is made of silicon, and the following seven types were used. Each tube was blocked with a clamp as its rear end in such a manner that the capacity thereof became the same, i.e., 14.13 cm³.

TABLE 1

| | Inner diameter of the tube (mm) | Length of the tube (cm) | Capacity of the tube (cm³) |
|---|---|---|---|
| 1 | 1.5 | 800 | 14.13 |
| 2 | 2.0 | 450 | 14.13 |
| 3 | 2.5 | 288 | 14.13 |
| 4 | 3.0 | 200 | 14.13 |
| 5 | 3.5 | 155 | 14.13 |
| 6 | 4.0 | 112.5 | 14.13 |
| 7 | 5.0 | 72 | 14.13 |

In this experiment, a handpiece 11 was fixed to a base, then a tubular tip 19, which is the tip of the handpiece 11, was inserted into a mock anterior chamber 31. The perfusate bottle 13 was disposed so that the fluid level 14a of a trap 14, which was attached to the perfusate supply tube 23, was at a height of 70 cm from the top of the tubular tip 19.

The experiment method is explained next. The perfusate was supplied in the tube 15 in the same manner as in Experiment 1 so that the air in the tube 15 would be compressed. Subsequently, general perfusion was conducted with the flow rate of the cataract surgical device 27 set at 30 cc/min and the maximum aspiration pressure set at 200 mmHg. After blocking the aspiration tube 29 with a clamp, the aspiration tube was opened when the aspiration pressure of the cataract surgical device 27 reached 200 mmHg. The change in the pressure of the mock anterior chamber 31 at this time was defined as the pressure change attributable to the surge occurrence. Table 2 shows the results.

TABLE 2

| | Pressure of the mock anterior chamber (mmHg) | | |
|---|---|---|---|
| Inner diameter of the tube (mm) | During normal perfusion | When the aspiration tube is blocked | During surge |
| Without tube | 59.5 | 38.8 | −33.8 |
| 1.5 | 61.3 | 41.6 | −18.4 |
| 2.0 | 61.3 | 41.6 | −8.5 |
| 2.5 | 61.8 | 42.1 | −4.3 |
| 3.0 | 60.9 | 39.3 | −2.9 |
| 3.5 | 60.9 | 41.6 | 4.8 |
| 4.0 | 60.9 | 42.1 | 8.3 |
| 5.0 | 61.3 | 42.6 | 3.2 |

Figure 12:
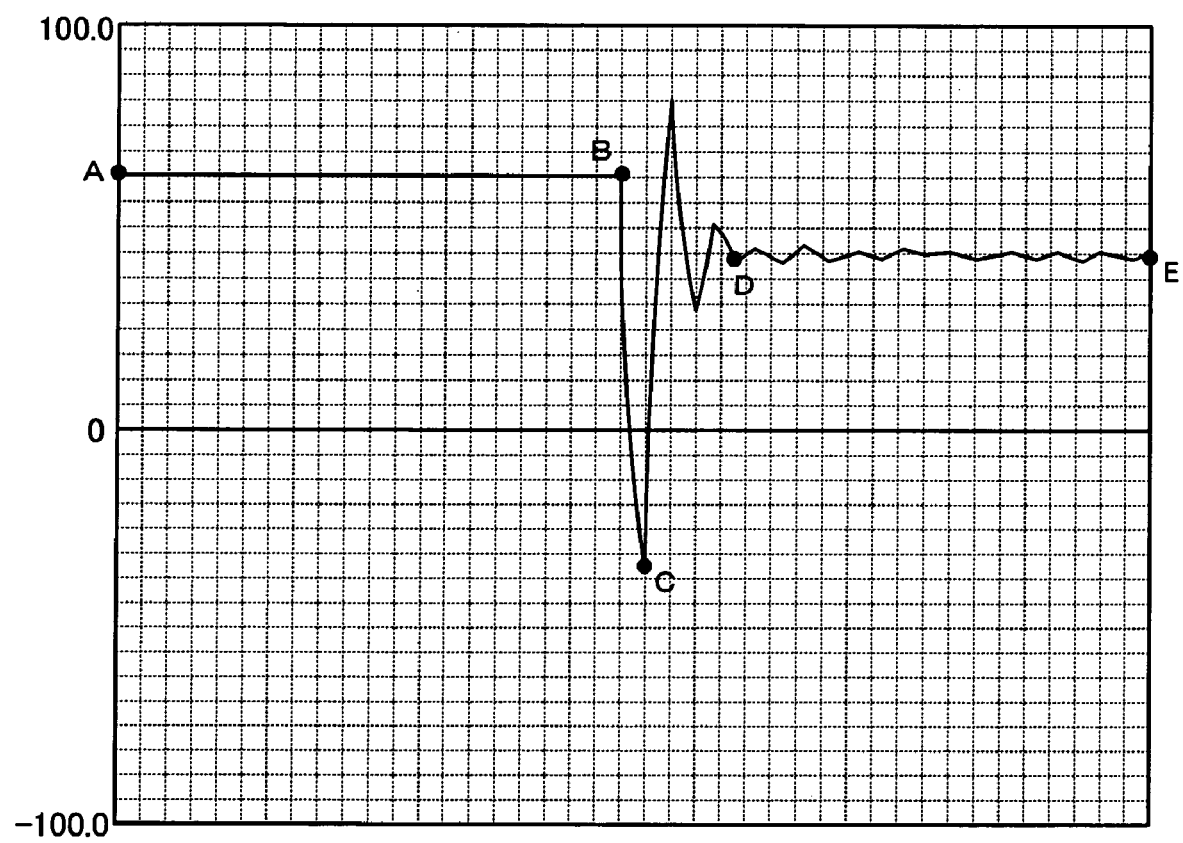
FIG. 12 is a graph showing the difference in pressure in a mock anterior chamber when no tube is provided.

The case wherein no tube 15 was provided is explained first. FIG. 12 is a graph showing the change in the pressure of the mock anterior chamber for this case. When an aspiration tube 23 was blocked with a clamp during normal perfusion, the perfusate was not aspirated and the pressure attributable to the difference in the height between the perfusate bottle 13 and the mock anterior chamber 31 directly affected the mock anterior chamber. Therefore, the pressure of the mock anterior chamber 31 became higher than that during normal perfusion. This condition is shown by the line between A-B in the graph. When the aspiration tube 29 was opened by removing the clamp, the perfusate was rapidly aspirated and the pressure of the mock anterior chamber 31 drastically decreased, as shown by the line B-C in the graph. At this time, the amount of perfusate flowing into the mock anterior chamber 31 could not catch up with the amount of perfusate aspirated from the mock anterior chamber 31, and therefore the pressure of the mock anterior chamber 31 became −33.8 mmHg (C), thus collapsing the mock anterior chamber 31. Thereafter, when the balance between the inflow rate (pressure) and the aspiration rate (pressure) of the perfusate became stable, the pressure gradually increased (between C-D) and returned to that of normal perfusion, i.e., about 59.5 mmHg (between D-E).

Figure 13:
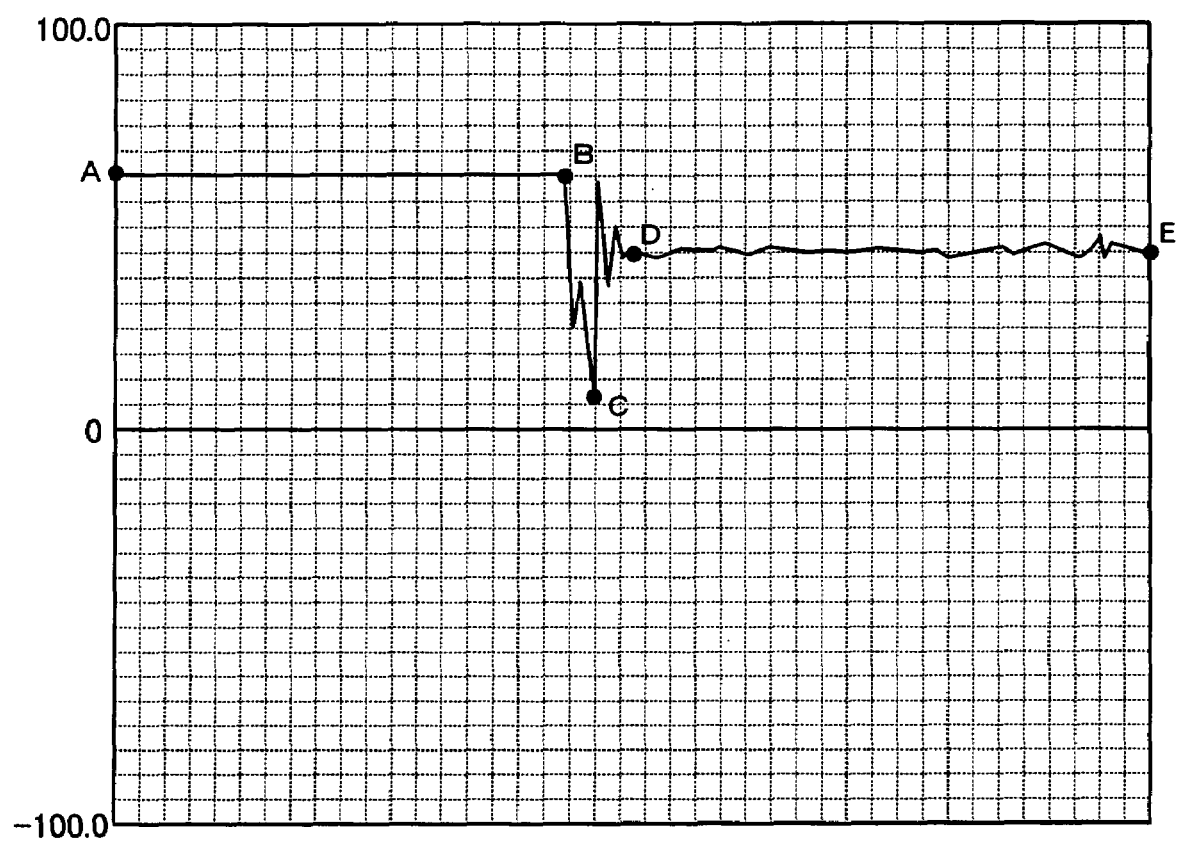
FIG. 13 is a graph showing the difference in pressure in a mock anterior chamber when a tube having an inner diameter of 4 mm is attached.

In contrast, for example, when the tube 15 having an inner diameter of 4 mm was attached, the phenomenon shown in FIG. 13 occurred. In other words, when the clamp blocking the aspiration tube 29 was removed and the perfusate was suddenly aspirated, the pressure of the mock anterior chamber 31 became negative. When the negative pressure was transferred to the tube 15, the compressed air in the tube 15 expanded and the perfusate stored in the tube 15 flowed into the mock anterior chamber 31. A rapid decrease in the pressure could thus be prevented because the perfusate flew from the tube 15 in accordance with the decrease in the pressure of the mock anterior chamber 31. When no tube 15 was provided, the pressure during the surge was −33.8 mmHg. In contrast, when a tube having an inner diameter of 4 mm was attached, the pressure became 8.3 mmHg (C). Therefore, it was possible to prevent the anterior chamber from collapsing.

As shown in Table 2 above, in this experiment, seven types of tube 15 having different inner diameters were used. Considering the fact that the inner diameter of the supply tube is 3 mm, when the inner diameter of the tube 15 was smaller than 3 mm, the pressure of the mock anterior chamber became negative during the surge, making it impossible to satisfactorily recover from the surge. Therefore, the diameter of the tube 15 should be larger than that of the supply tube. However, when the inner diameter of the tube was 5 mm, although the pressure of the mock anterior chamber during the surge was not negative, the pressure was greatly decreased compared to the case where a tube 15 having an inner diameter of 4 mm was used, so it is undesirable to further enlarge the inner diameter of the tube. When the inner diameter of the supply tube 23 is 3 mm, it is preferable that the inner diameter of the tube 15 be not less than 3.5 mm and not greater than 5 mm, and most preferably that it be 4 mm.

Expressing this as a ratio between the inner diameter of the supply tube 23 and the inner diameter of the tube 15, which serves as a decompression-compensating instrument, the inner diameter of the tube 15 is preferably 1.17 times as large as the inner diameter of the supply tube 23, more preferably 1.67 times and most preferably 1.33 times as large as the inner diameter of the supply tube 23.

(c) Experiment 3

Given below is a comparison between the effects achieved by a tube of the present invention and those achieved by a spherical chamber disclosed in EP Patent No. 0180317 and U.S. Pat. No. 4,841,984.

Experiment 3-1

Using an experimental apparatus as shown in FIG. 6, an experiment was conducted in which a tube 15 having an inner diameter of 4 mm and a length of 160 cm was used (the present example) and an elastic spherical chamber having a diameter of 5 cm or 6.5 cm was used instead of the tube 15 (Comparative Examples), wherein each tube and spherical chamber was connected to a joint tube 21. On the assumption that a surge would occur immediately after the start of surgery, the aspiration tube was blocked immediately after the start of aspiration. When the pressure of the mock anterior chamber became the maximum level, i.e., when the pressure gauge of the cataract surgical device 27 indicated an aspiration pressure of 300 mmHg (about one second after blocking the aspiration tube), the blockage of the tube was removed, and the change in the pressure of the mock anterior chamber was measured. The SOVEREIGN® phacoemulsification system (manufactured by Allergan Inc.) was used as the cataract surgical device 27. The conditions were as follows: a bottle height of 40 cm (about 72 cm from the end of the tip to the surface of the fluid), an aspiration flow rate of 40 cc/min, and a maximum aspiration pressure of 300 mmHg.

Figure 14:
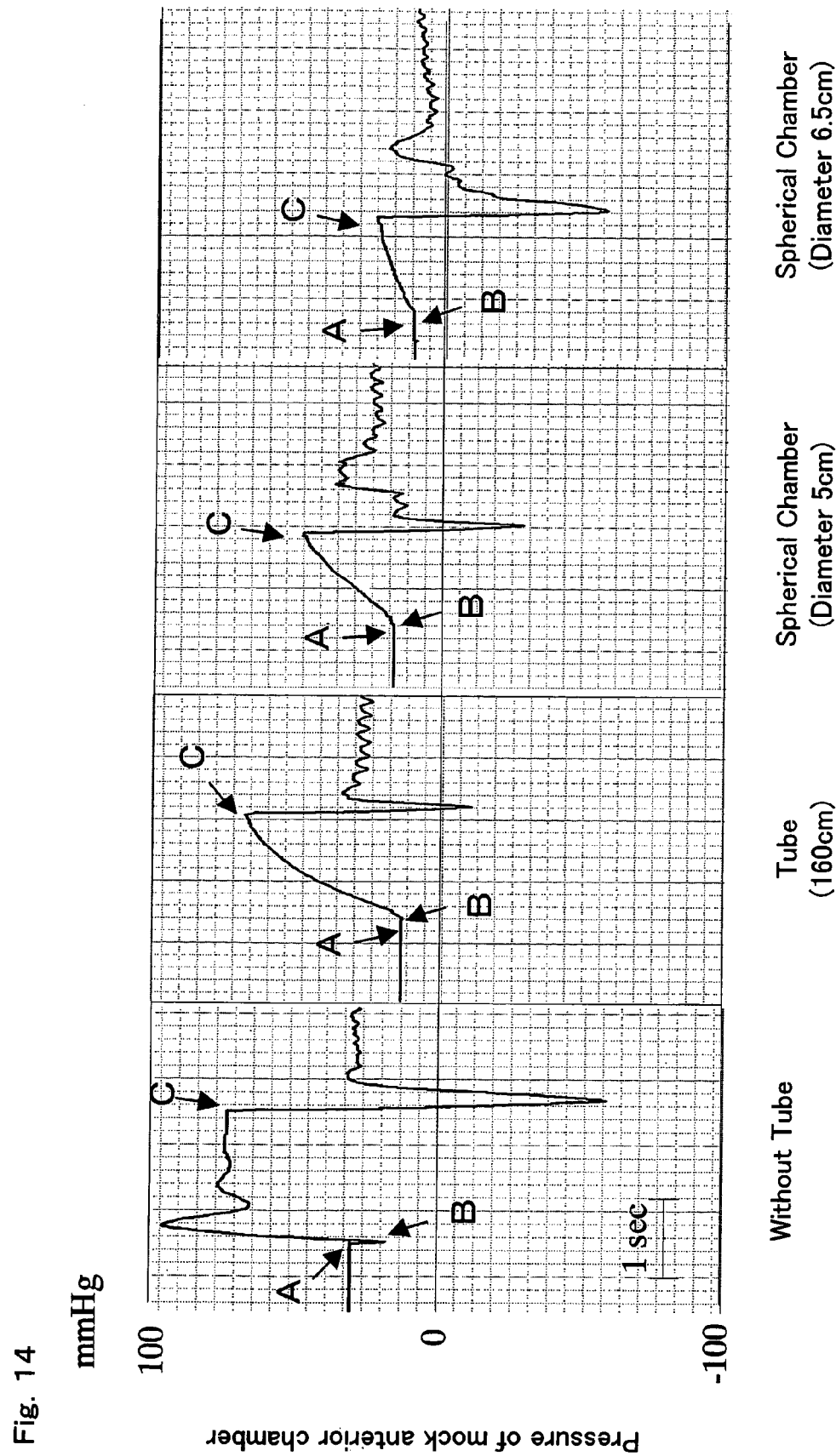
FIG. 14 is a graph showing the difference in pressure in a mock anterior chamber when a tube and a spherical chamber are attached.

FIG. 14 shows the results. Table 3 shows the pressure of the mock anterior chamber 31 during a surge.

TABLE 3

| Decompression-compensating instrument | Pressure of the mock anterior chamber during a surge (mmHg) |
|---|---|
| Without tube or spherical chamber | −58.1 |
| Tube (160 cm) | −9.6 |
| Spherical chamber (diameter of 5 cm) | −26.8 |
| Spherical chamber (diameter of 6.5 cm) | −55.7 |

Regarding the pressure of the mock anterior chamber 31 during the blockage of the aspiration tube and after recovery from the surge, there was no significant difference between the cases where no tube was provided and where the tube of the present invention was used. In contrast, when a spherical chamber was used, both the pressure of the mock anterior chamber 31 during the blockage of the aspiration tube and that after recovery from the surge were lower than those in the case where no tube was provided, and the larger the diameter, the lower the pressure. It is assumed that this is because the pressure of the mock anterior chamber 31 is alleviated by the tube or spherical chamber when either is provided in addition to the perfusion channel; however, in the spherical chamber, the extent of the alleviation changes depending on the capacity of the sphere and the area of the interface between the stored fluid and the air layer. In other words, in the tube of the present invention, the interface between the stored fluid and the air layer (sectional area of the tube) was small, and the air pressure easily affected the perfusate.

When neither a tube nor a spherical chamber was provided, the pressure of the mock anterior chamber 31 during a surge was −58.1 mmHg. In contrast, when the tube of the present invention was provided, the pressure thereof was −9.6 mmHg. It was found that the extent of the surge became extremely small when a tube of the present invention was used. When a spherical chamber having a diameter of 5 cm was used, the pressure became −26.8 mmHg, and when a spherical chamber having a diameter of 6.5 cm was used, the pressure became −55.7 mmHg. Therefore, the extent of the surge was reduced compared to a case when neither a tube nor a spherical chamber was provided; however, the extent of the reduction was significantly lower than the case in which the tube of the present invention was used. When a spherical chamber was used, a phenomenon was observed wherein the pressure of the mock anterior chamber 31 raised at the point 0.7 to 0.8 second after the surge. It is assumed that the reason for this is that when the perfusate stored in the spherical chamber flowed into the mock anterior chamber 31 during the surge, a whirlpool was generated in the spherical chamber and air also flowed in with the perfusate. It is assumed that this whirlpool phenomenon was also attributable to the fact that the area of the interface between the perfusate and the air layer in the spherical chamber is large. Such, an inflow of air may damage tissues in the eye.

Experiment 3-2

The next experiment was conducted on the assumption that a surge would occur five seconds after the start of surgery. The experiment was conducted in the same manner as Experiment 2-1 except that the tube was blocked five seconds after the start of surgery. A tube having an inner diameter of 4 mm and a length of 160 cm, and a spherical chamber having a diameter of 5 cm, 6.5 cm or 7.5 cm were used. Table 4 shows the results.

TABLE 4

| Tube or spherical chamber | | Pressure of the mock anterior chamber (mmHg) | | | |
|---|---|---|---|---|---|
| | | Aspiration tube | | Surge | |
| | | Before blockage | During blockage | During occurrence | After recovery |
| Neither a tube nor a spherical chamber was provided | | 27.2 | 74.1 | −37.3 | 27.9 |
| Tube (160 cm) | | 24.1 | 71.4 | −14.5 | 26.3 |
| Spherical chamber | Diameter of 5 cm | 24.8 | 66.5 | −27.4 | 27.2 |
| | Diameter of 6.5 cm | 11.9 | 50.7 | −27.4 | 19.6 |
| | Diameter of 7.5 cm | 5.7 | 43.6 | −30.5 | 12.8 |

As shown in Table 4, the pressure of the mock anterior chamber 31 during the surge was −37.3 mmHg when neither a tube nor a spherical chamber was provided, and the pressure was −14.5 mmHg when the tube of the present invention was used. Therefore, the pressure reduction in the mock anterior chamber 31 was significantly lessened by using the tube of the present invention. In contrast, when a spherical chamber was used, the pressure of the mock anterior chamber 31 was −27.4 mmHg, −27.4 mmHg or −30.5 mmHg when the diameter of the spherical chamber was 5 cm, 6.5 cm or 7.5 cm, respectively. Therefore, the reduction of the pressure was somewhat restricted, but the effect was significantly less than that achieved by the tube of the present invention.

Figure 15:
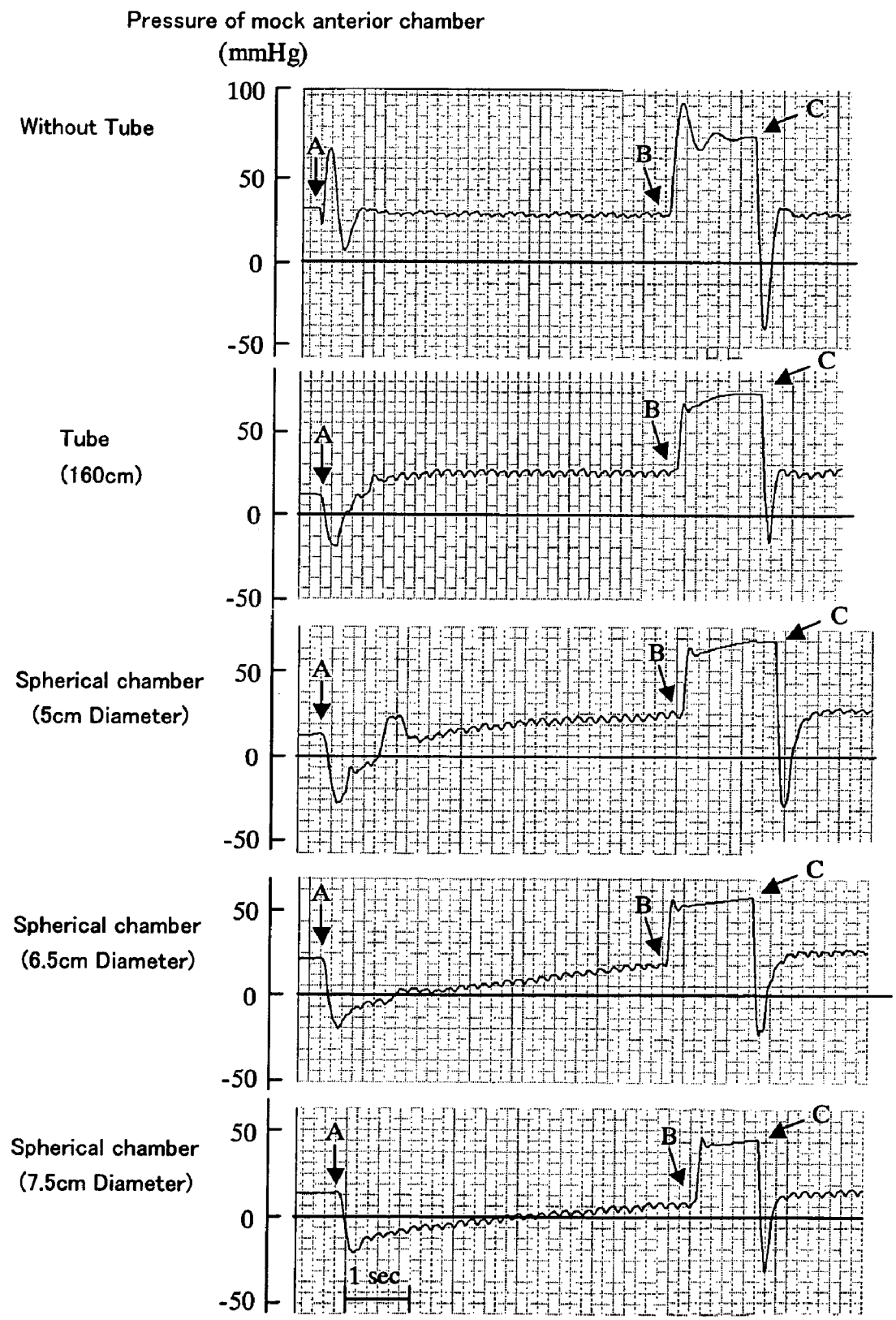
FIG. 15 is a graph showing the difference in pressure in a mock anterior chamber when a tube and a spherical chamber are attached.
Figure 16:
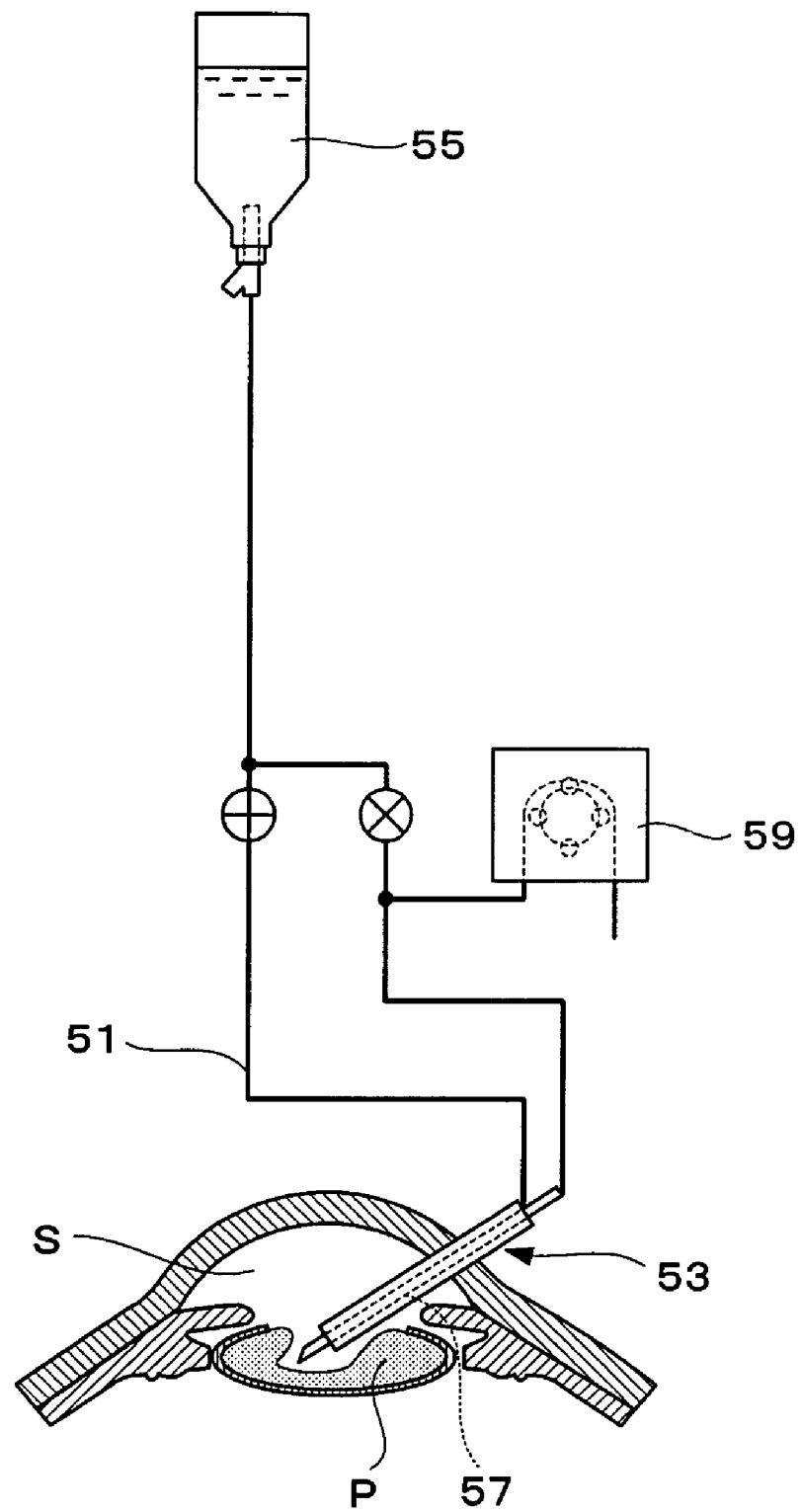
FIG. 16 illustrates a conventional surgical apparatus used in a cataract surgical operation.
Figure 17:
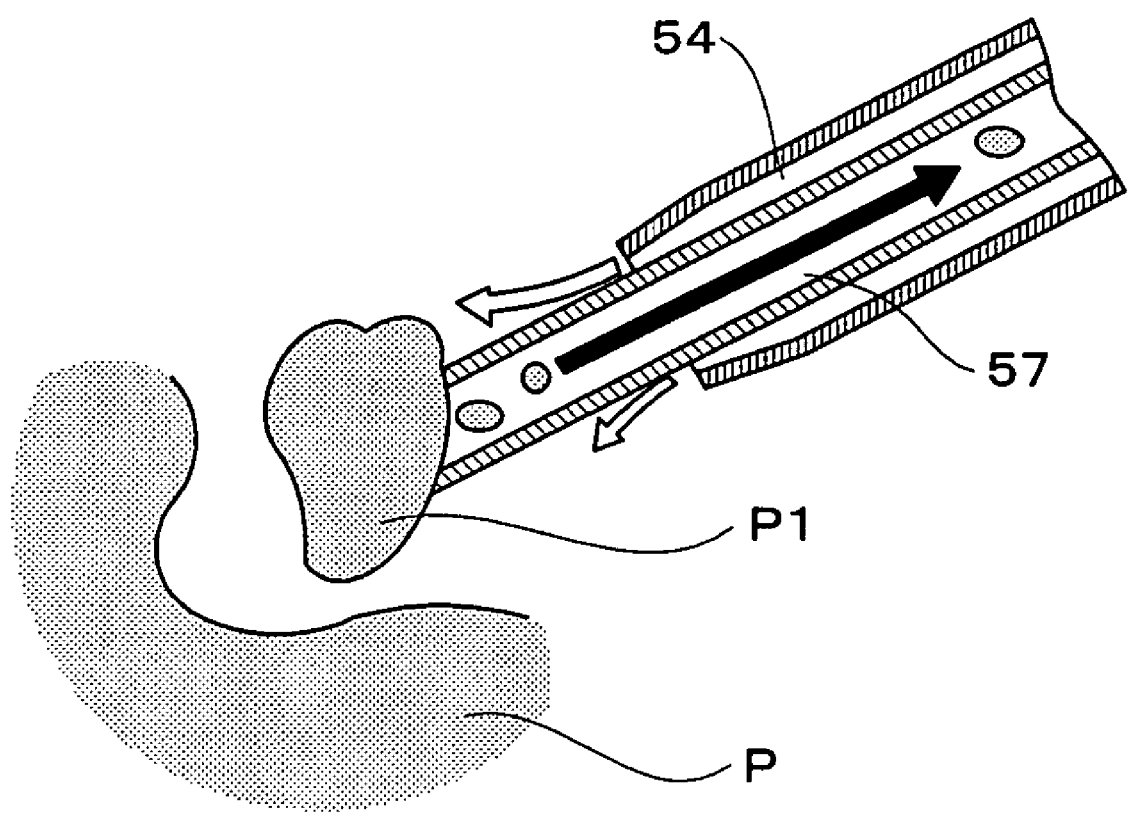
FIG. 17 is a diagram illustrating a surge.

FIG. 15 shows the change in the pressure of the mock anterior chamber over the elapsed time. According to this figure, the pressure of the mock anterior chamber 31 immediately after the start of aspiration was extremely low when a spherical chamber was used. In particular, when a spherical chamber having a diameter of 6 cm or 7.5 cm was used, the pressure of the mock anterior chamber 31 became negative for about 2 to 3 seconds from the start of aspiration. When those spherical chambers were used, the pressure of the mock anterior chamber 31 rose with the passage of time; however, depending on the diameter of the spherical chamber, even five seconds after the start of aspiration (before blocking the aspiration tube), the pressure did not reach the ordinary level of pressure in the anterior chamber during surgery.

Using a spherical chamber having a diameter of 7.5 cm, the elapsed time was measured until the pressure of the mock anterior chamber became the same level as the case where neither a tube nor a spherical chamber was used. As a result, it was found that it took about 27 to 30 seconds from the start of aspiration. This result indicates that spherical chambers cannot practically be used because it is disadvantageous to conduct surgery before the pressure in the anterior chamber reaches a steady level.

Several embodiments of the present invention are described above; however, a person skilled in the art would be able to add various modifications and changes within a range not departing from the scope of the novel teachings and effects of the present invention, and therefore, such modifications and changes are included in the scope of the present invention defined by the Claims.

The present application is based on Japanese Patent Application No. 2002-182045 filed with the Japan Patent Office, and the entire content of that application is included in the present specification.

The invention claimed is:

1. An intraocular surgical apparatus comprising:
a main body that can be held in a surgeon's hand,
the main body further comprising:
a pulverizing member that is attached at one end of the main body and that pulverizes a predetermined affected tissue;
an inlet channel that supplies perfusate to the vicinity of the pulverizing member;
an aspiration channel for aspirating the affected tissue that has been pulverized by the pulverizing member; and
a decompression-compensating instrument that is for use in intraocular surgery and is connected to a point midway along the inlet channel, the decompression-compensating instrument comnrising:
a storage member, having a capacity of 7 cm$^3$ to 22 cm$^3$, connectable to a point midway along the supply channel,
wherein the storage member forms a chamber that is closable except for an opening from which the perfusate that is to be supplied to the supply channel flows;
the decompression-compensating instrument supplies the perfusate into the affected part when the internal pressure of the affected part is excessively lowered, the perfusate being supplied from the storage member,
whereby a rapid decrease in an inflow rate thereafter is prevented.

2. An intraocular surgical apparatus according to claim 1, wherein the decompression-compensating instrument is detachably mounted on the main body.

3. An intraocular surgical apparatus according to claim 2, wherein the storage member of the decompression-compensating instrument is composed of a tube having the opening at one end, the tube being wound around the main body.

4. An intraocular surgical apparatus according to claim 2, wherein the storage member of the decompression-compensating instrument is mounted on the distal end of the main body along the longitudinal direction of the main body.

5. An intraocular surgical apparatus according to claim 1, wherein the storage member of the decompression-compensating instrument is composed of a tube having the opening at one end, the tube being wound around the main body.

6. An intraocular surgical apparatus according to claim 1, wherein the storage member of the decompression-compensating instrument is mounted on the distal end of the main body along the longitudinal direction of the main body.

7. An intraocular surgical apparatus comprising
a main body that can be held in a surgeon's hand,
the main body further comprising:
a pulverizing member that is attached at one end of the main body and that pulverizes a predetermined affected tissue;
an inlet channel that supplies perfusate to the vicinity of the pulverizing member;
an aspiration channel for aspirating the affected tissue that has been pulverized by the pulverizing member; and
a decompression-compensating instrument that is for use in intraocular surgery and is connected to a point midway along the inlet channel, the decompression-compensating instrument comprising:
a storage member, having a capacity of 7 $cm^3$ to 22 $cm^3$, connectable to a point midway along the supply channel.
wherein the storage member is composed of a tube that is closable except for an opening at one end from which the perfusate that is to be supplied to the supply channel flows;
the decompression-compensating instrument supplies the perfusate into the affected part when the internal pressure of the affected part is excessively lowered, the perfusate being supplied from the storage member,
whereby a rapid decrease in an inflow rate thereafter is prevented.

8. An intraocular surgical apparatus according to claim 7, wherein the decompression-compensating instrument is detachably mounted on the main body.

9. An intraocular surgical apparatus according to claim 8, wherein the storage member of the decompression-compensating instrument is composed of a tube having the opening at one end, the tube being wound around the main body.

10. An intraocular surgical apparatus according to claim 8, wherein the storage member of the decompression-compensating instrument is mounted on the other end of the main body along the longitudinal direction of the main body.

11. An intraocular surgical apparatus according to claim 7, wherein the storage member of the decompression-compensating instrument is composed of a tube having the opening at one end, the tube being wound around the main body.

12. An intraocular surgical apparatus according to claim 7, wherein the storage member of the decompression-compensating instrument is mounted on the distal end of the main body along the longitudinal direction of the main body.

13. A method for intraocular surgery, wherein a perfusate is supplied into an affected part of an eye via a supply channel at a predetermined pressure, while the perfusate is aspirated via an aspiration channel together with the affected tissue that is to be removed, the method comprising the steps of:
providing a decompression-compensating instrument for use in intraocular surgery, the decompression-compensating instrument comprising a storage member, having a capacity of 7 $cm^3$ to 22 $cm^3$, connectable to a point midway along the supply channel, wherein the storage member forms a chamber that is closable except for an opening from which the perfusate that is to be supplied to the supply channel flows, and the decompression-compensating instrument supplies the perfusate into the affected part when the internal pressure of the affected part is excessively lowered, the perfusate being supplied from the storage member, whereby a rapid decrease in an inflow rate thereafter is prevented;
making the storage member and the supply channel communicate with each other via the opening by connecting the decompression-compensating instrument to a point midway along the supply channel, with air contained in the storage member;
supplying the perfusate to the supply channel, flowing the perfusate into the storage member via the supply tube, and containing the perfusate in the storage member under pressure of the air; and
supplying the perfusate into the affected part of the eye while aspirating the affected tissue from the eye together with the perfusate.

14. A method for intraocular surgery according to claim 13, wherein, when the intraocular pressure rapidly lowers, the perfusate stored in the storage member is supplied to the eye via the supply channel by the effect of the air pressure.

15. A method for intraocular surgery according to claim 13, wherein the storage member is composed of a tube having the opening at one end.

16. A method for intraocular surgery according to claim 15, wherein the inner diameter of the tube is not less than 1.1 times and not more than 1.7 times as large as the inner diameter of the supply channel in the portion upstream from the point to which the tube is connected.

17. A method for intraocular surgery according to claim 15, wherein the inner diameter of the tube is not smaller than 3.5 mm and not greater than 5.0 mm.

* * * * *